(12) United States Patent
Numajiri

(10) Patent No.: US 6,699,198 B2
(45) Date of Patent: Mar. 2, 2004

(54) OCULAR-BLOOD-FLOW METER

(75) Inventor: Yasuyuki Numajiri, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 33 days.

(21) Appl. No.: 09/879,180

(22) Filed: Jun. 13, 2001

(65) Prior Publication Data

US 2002/0045834 A1 Apr. 18, 2002

(30) Foreign Application Priority Data

Jun. 14, 2000 (JP) .......................... 2000-178182
Sep. 25, 2000 (JP) .......................... 2000-290419

(51) Int. Cl.⁷ .............................................. A61B 5/02
(52) U.S. Cl. ................ 600/504; 600/318; 600/476; 600/478; 600/479; 600/480; 600/558; 351/200; 351/221
(58) Field of Search ........................ 351/221, 200; 600/476, 478, 481, 504, 318, 558, 479, 480

(56) References Cited

U.S. PATENT DOCUMENTS

| | | | |
|---|---|---|---|
| 4,346,991 A | * 8/1982 | Gardner et al. ............ 356/28.5 |
| 4,830,483 A | 5/1989 | Kohayakawa et al. ...... 351/221 |
| 4,856,891 A | 8/1989 | Pflibsen et al. ............ 351/210 |
| 4,866,243 A | 9/1989 | Sakane et al. ......... 219/121.62 |
| 5,106,184 A | * 4/1992 | Milbocker .................. 351/221 |
| 5,615,683 A | * 4/1997 | Toge et al. .................. 600/479 |
| 5,640,963 A | 6/1997 | Tanaka ........................ 128/665 |
| 5,894,337 A | 4/1999 | Okinishi et al. ............ 351/205 |
| 6,192,269 B1 | 2/2001 | Okumura et al. ........... 600/479 |
| 6,324,420 B1 | * 11/2001 | Kishida et al. .............. 600/479 |
| 6,411,839 B1 | * 6/2002 | Okinishi ...................... 600/479 |

FOREIGN PATENT DOCUMENTS

JP 10-71126 3/1998

* cited by examiner

Primary Examiner—Marvin M. Lateef
Assistant Examiner—Jeoyuh Lin
(74) Attorney, Agent, or Firm—Fitzpatrick, Cella, Harper & Scinto

(57) ABSTRACT

An ocular blood-flow meter includes an optical system for applying measuring light to a blood vessel of a subject eye, and for receiving light scattered by the blood vessel of the subject eye. A mechanism is provided for changing a direction in which the measuring light is applied and a direction in which the scattered light is received so as to enable a plurality of measurements in different directions. A controller performs the plurality of measurements in the different directions by using the optical system and the mechanism so as to obtain information concerning a blood flow. An output device provides a received-light signal obtained by the optical system or the information concerning the blood flow. An input device enables an operator to select a re-measurement operation in a desired direction from the different directions and to instruct the selected re-measurement operation.

66 Claims, 10 Drawing Sheets

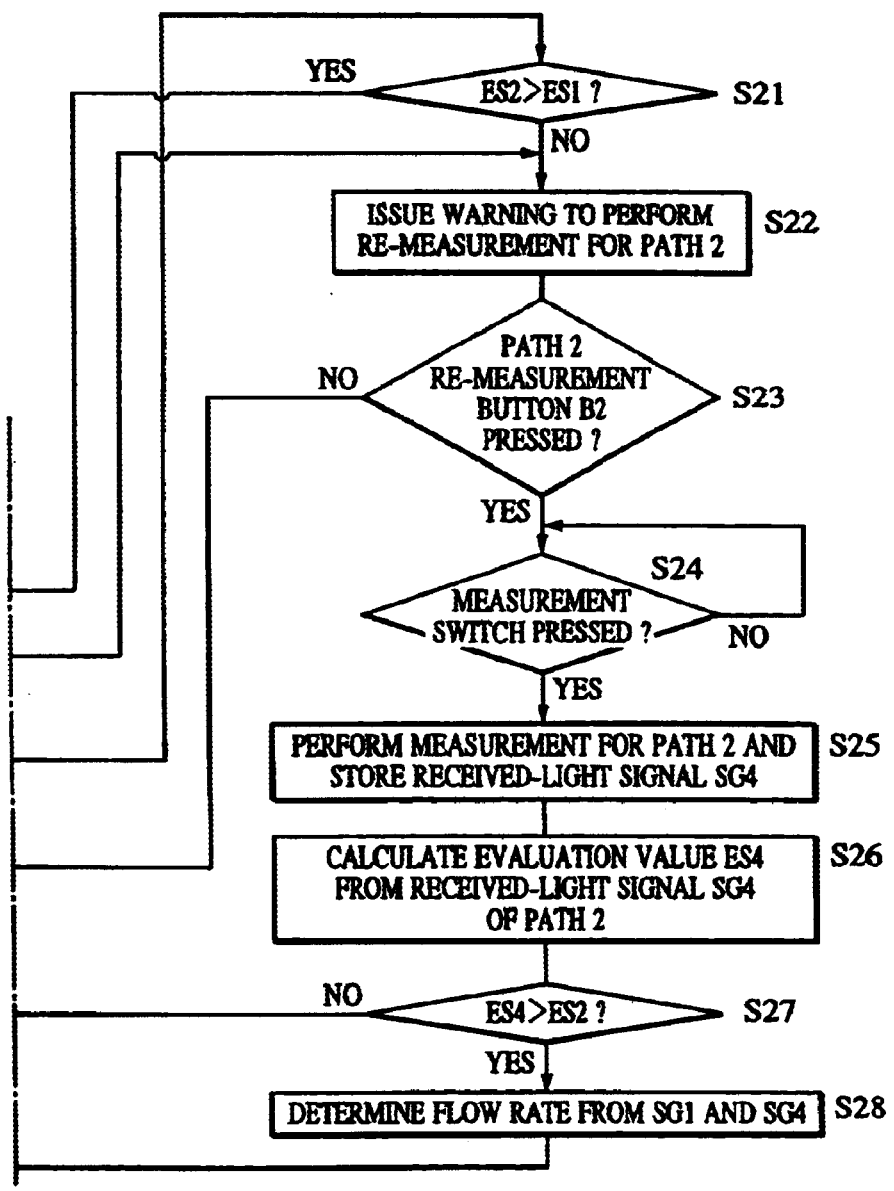

OCULAR-BLOOD-FLOW METER

BACKGROUND OF THE INVENTION

1. Field of the Invention

The present invention generally relates to an ocular blood-flow meter for measuring the flow rate of blood in a blood vessel of a patient's eye.

2. Description of the Related Art

An ocular blood-flow meter utilizing the Doppler effect determines the flow rate of blood in the following manner. A laser beam is applied to a blood vessel of a subject eye, and the light scattered and reflected by the blood vessel is received by a photodetector. Then, an interference signal of a Doppler shift component, i.e., the light scattered and reflected by the blood flow, and the light scattered and reflected by a stationary blood-vessel wall is detected. Upon analyzing the frequency of the interference signal, the blood-flow rate is determined. That is, the blood-flow rate (maximum rate $V_{max}$) is determined according to the following equation:

$$V_{max} = \{\lambda/(n \cdot \alpha)\} \cdot \||\Delta f_{max1}| - |\Delta f_{max2}|\|/\cos\beta \qquad (1)$$

wherein $\Delta f_{max1}$ and $\Delta f_{max2}$ indicate the maximum frequency shifts calculated from the received-light signals received by two photodetectors; $\lambda$ represents the wavelength of the laser light; n designates the index of refraction of a portion to be examined; a indicates the angle between the two light-detecting optical axes within the eye; and $\beta$ represents the angle between the plane formed by the two light-detecting optical axes and the velocity vector of the blood flow. By measuring the flow rates from the two directions as discussed above, contributions due to the directions of incidence of the measuring beams are canceled, thereby making it possible to measure the flow rate of blood at a certain portion on the eye fundus. By matching the line of intersection between the plane formed by the two light-detecting optical axes and the eye fundus to the angle $\beta$, $\beta$ becomes 0 degrees, thereby measuring the true maximum flow rate.

In measuring the flow rate with an ocular blood-flow meter, if the relative position of an optical system of the ocular blood-flow meter with respect to a portion of the eye to be examined is changed due to involuntary eye movement, it becomes difficult to perform precise measurements. In order to solve this problem, U.S. Pat. No. 4,856, 891 discloses a tracking device. As described in this patent, a beam of light is applied from a tracking light source to a subject vessel, and the resulting blood-vessel image is captured by a charge-coupled device (CCD) camera. Then, the tracking device performs tracking by scanning the beam of light from the tracking light source so that the blood vessel image can be stabilized at a fixed position of the CCD camera in accordance with the eye movement.

However, the maximum value $\Delta f_{max1}$ of the Doppler shift in equation (1) is detected as an interference signal between the Doppler component shifted by the flow of blood and the stationary vessel wall. Thus, the maximum frequency shift $\Delta f_{max}$ obtained by analyzing the frequencies lacks sign information since what is measured is $|\Delta f_{max}|$. In measuring the flow rates in different portions of the eye fundus, the signs of the maximum frequency shifts $\Delta f_{max1}$ and $\Delta f_{max2}$ may both be positive, or they may both be negative, or one value may be positive and the other value may be negative. Accordingly, the maximum flow rate $V_{max}$ cannot be determined for some portions according to equation (1).

U.S. Pat. No. 5,640,963 discloses an eye-fundus-blood-flow meter provided with a mechanism for switching the directions of incidence of the light beams in order to precisely measure the flow rate of blood regardless of the eye-fundus-vessel portion measured or the direction of the eye fundus vessel. However, there is still room for improvement in this flow meter. That is, when measurements are performed in a single direction of incidence, the patient's eyelashes may eclipse the beam of light, or a displacement in the alignment or blinking, or a poor fixation point may be selected, thereby causing a failure to perform correct measurement in this direction of incidence. Due to the incorrect measurement in this direction, even if a correct measurement is performed in the other direction, it is determined that measurements are incorrectly performed in both directions, thereby wasting the measurement of correctly measured paths. Additionally, after performing re-alignment, measurements must be performed once again in both directions of incidence, thereby subjecting a patient to a long measurement time.

SUMMARY OF THE INVENTION

Accordingly, it is an object of the present invention to improve a conventional eye-fundus-blood-flow meter, and more specifically, to provide a highly precise and easy-to-use ocular blood-flow meter in which it can be easily determine whether measurements should be repeated.

In order to achieve the above objects, according to one aspect of the present invention, there is provided an ocular blood-flow meter comprising an optical system configured and positioned to apply measuring light to a blood vessel of a subject eye, and to receive light scattered by the blood vessel of the subject eye. The meter also comprises a mechanism configured and positioned to change the direction in which the measuring light is applied to the blood vessel or the direction in which the scattered light is received by at least a portion of the optical system so as to enable a plurality of measurements of the blood flow in the blood vessel using measuring light applied to the blood vessel in different directions or using scattered light received by at least a portion of the optical system in different directions. The meter further comprises a device configured and positioned to receive the scattered light from the optical system. The device outputs a received-light signal containing information on blood flow in the blood vessel in response to receiving the scattered light from the optical system. In addition, the meter comprises a controller connected to the device to receive the received-light signal and configured to perform the plurality of measurements of the blood flow in the blood vessel using the received-light signal generated from measuring light being applied to the blood vessel in different directions and scattered by the blood vessel or generated from the scattered light received by at least a portion of the optical system in different directions. The controller is also configured to perform a re-measurement operation to re-measure the blood flow in the blood vessel using a received-light signal generated from measuring light being applied to the blood vessel in a desired direction and then scattered by the blood vessel or generated from the scattered light received by at least a portion of the optical system in a desired direction in response to an instruction by an operator to perform a re-measurement operation in the desired direction. In addition, the meter comprises an input device. The input device is electrically coupled to the controller. The input device is configured to enable an operator to select a re-measurement operation to re-measure the blood flow in the blood vessel using a received-light signal generated from measuring light being applied to the blood vessel in a desired direction and then scattered by the blood vessel or generated from the scattered light received by at least a portion of the optical system in a desired direction. The input device also is configured to instruct the controller to perform the selected re-measurement operation selected by the operator.

According to another aspect, the present invention that achieves at least one of these objectives relates to an ocular blood-flow meter comprising an optical system configured and positioned to apply measuring light to a blood vessel of a subject eye, and to receive light scattered by the blood vessel of the subject eye. The meter also comprises a mechanism configured and positioned to change the direction in which the measuring light is applied to the blood vessel or the direction in which the scattered light is received by at least a portion of the optical system so as to enable a plurality of measurements of the blood flow in the blood vessel using measuring light applied to the blood vessel in different directions or using scattered light received by at least a portion of the optical system in different directions. In addition, the meter comprises a controller configured to perform the plurality of measurements of the blood flow in the blood vessel using the measuring light being applied to the blood vessel in different directions and scattered by the blood vessel or using the scattered light received by at least a portion of the optical system in different directions. The controller is also configured to perform a re-measurement operation to re-measure the blood flow in the blood vessel using measuring light being applied to the blood vessel in a desired direction and then scattered by the blood vessel or using scattered light received by at least a portion of the optical system in a desired direction. The controller is also configured to determine whether a re-measurement operation is required. The meter further includes an output device connected to the controller. The output device is configured to present information to an operator indicating whether re-measurement is required in response to the controller determining that a re-measurement operation is required.

According to still another aspect, the present invention that achieves at least one of these objectives relates to an ocular blood-flow meter comprising optical means for applying measuring light to a blood vessel of a subject eye, and for receiving light scattered by the blood vessel of the subject eye. The meter also includes direction-changing means for changing the direction in which the measuring light is applied to the blood vessel or the direction in which the scattered light is received by at least a portion of the optical means so as to enable a plurality of measurements of the blood flow in the blood vessel using measuring light applied to the blood vessel in different directions or using scattered light received by at least a portion of the optical means in different directions. In addition, the meter includes signal-outputting means for outputting a received-light signal containing information on blood flow in the blood vessel in response to receiving the scattered light from the optical means. Also, the meter includes control means for performing the plurality of measurements of the blood flow in the blood vessel using the received-light signal generated from measuring light being applied to the blood vessel in different directions and scattered by the blood vessel or generated from the scattered light received by at least a portion of the optical means in different directions. The control means comprises means for performing a re-measurement operation to re-measure the blood flow in the blood vessel using a received-light signal generated from measuring light being applied to the blood vessel in a desired direction and then scattered by the blood vessel or generated from the scattered light received by at least a portion of the optical means in a desired direction in response to an instruction by an operator to perform a re-measurement operation in the desired direction. The meter also includes input means for enabling an operator to select a re-measurement operation to re-measure the blood flow in the blood vessel using a received-light signal generated from measuring light being applied to the blood vessel in a desired direction and then scattered by the blood vessel or generated from the scattered light received by at least a portion of the optical means in a desired direction. The input means comprises means for instructing the control means to perform the selected re-measurement operation selected by the operator.

According to still another aspect, the present invention that achieves at least one of these objectives relates to an ocular blood-flow meter comprising optical means for applying measuring light to a blood vessel of a subject eye, and for receiving light scattered by the blood vessel of the subject eye. The meter also comprises direction-changing means for changing the direction in which the measuring light is applied to the blood vessel or the direction in which the scattered light is received by at least a portion of the optical means so as to enable a plurality of measurements of the blood flow in the blood vessel using measuring light applied to the blood vessel in different directions or using scattered light received by at least a portion of the optical means in different directions. The meter further includes control means for performing the plurality of measurements of the blood flow in the blood vessel using the measuring light being applied to the blood vessel in different directions and scattered by the blood vessel or using the scattered light received by at least a portion of the optical means in different directions. The control means comprises means for performing a re-measurement operation to re-measure the blood flow in the blood vessel using measuring light being applied to the blood vessel in a desired direction and then scattered by the blood vessel or using scattered light received by at least a portion of the optical means in a desired direction. The control means also comprises means for determining whether a re-measurement operation is required. The meter further comprises output means for presenting information to an operator indicating whether re-measurement is required in response to the control means determining that a re-measurement operation is required.

According to still another aspect, the present invention that achieves at least one of these objectives relates to a method of measuring ocular blood flow in an ocular blood vessel comprising the steps of applying measuring light to a blood vessel of a subject eye, receiving light scattered by the blood vessel of the subject eye, changing the direction in which the measuring light is applied to the blood vessel in the applying step or the direction in which the scattered light is received in the receiving step so as to enable the performing of a plurality of measurements of the blood flow in the blood vessel using measuring light applied to the blood vessel in different directions or using scattered light received in different directions, outputting a received-light signal containing information on blood flow in the blood vessel generated from the scattered light received in the receiving step, performing the plurality of measurements of the blood flow in the blood vessel using the received-light signal generated from measuring light being applied to the blood vessel in different directions and scattered by the blood vessel or generated from the scattered light received in different directions, and performing a re-measurement operation to re-measure the blood flow in the blood vessel using a received-light signal generated from measuring light being applied to the blood vessel in a desired direction and then scattered by the blood vessel or generated from the scattered light received in a desired direction in response to an instruction by an operator to perform a re-measurement operation in the desired direction.

According to still another aspect, the present invention that achieves at least one of these objectives relates to a method of determining the ocular blood flow in an ocular blood vessel comprising the steps of applying measuring light to a blood vessel of a subject eye, receiving light scattered by the blood vessel of the subject eye, changing the direction in which the measuring light is applied to the blood vessel in the applying step or the direction in which the scattered light is received in the receiving step so as to enable a plurality of measurements of the blood flow in the blood vessel using measuring light applied to the blood vessel in different directions or using scattered light received in different directions, performing the plurality of measurements of the blood flow in the blood vessel using the measuring light being applied to the blood vessel in different directions and scattered by the blood vessel or using the scattered light received in different directions, performing a re-measurement operation to re-measure the blood flow in the blood vessel using measuring light being applied to the blood vessel in a desired direction and then scattered by the blood vessel or using scattered light received in a desired direction, determining whether a re-measurement operation is required, and presenting information to an operator indicating whether re-measurement is required in response to the determining step determining that a re-measurement operation is required.

Further objects, features and advantages of the present invention will become apparent from the following description of the preferred embodiments with reference to the attached drawings.

BRIEF DESCRIPTION OF THE DRAWINGS

FIG. 13 shows the relationship between FIGS. 13A and 13B. FIGS. 13A and 13B are a flow chart illustrating the operation of a third embodiment of the present invention.

DESCRIPTION OF THE PREFERRED EMBODIMENTS

First Embodiment

Figure 1:
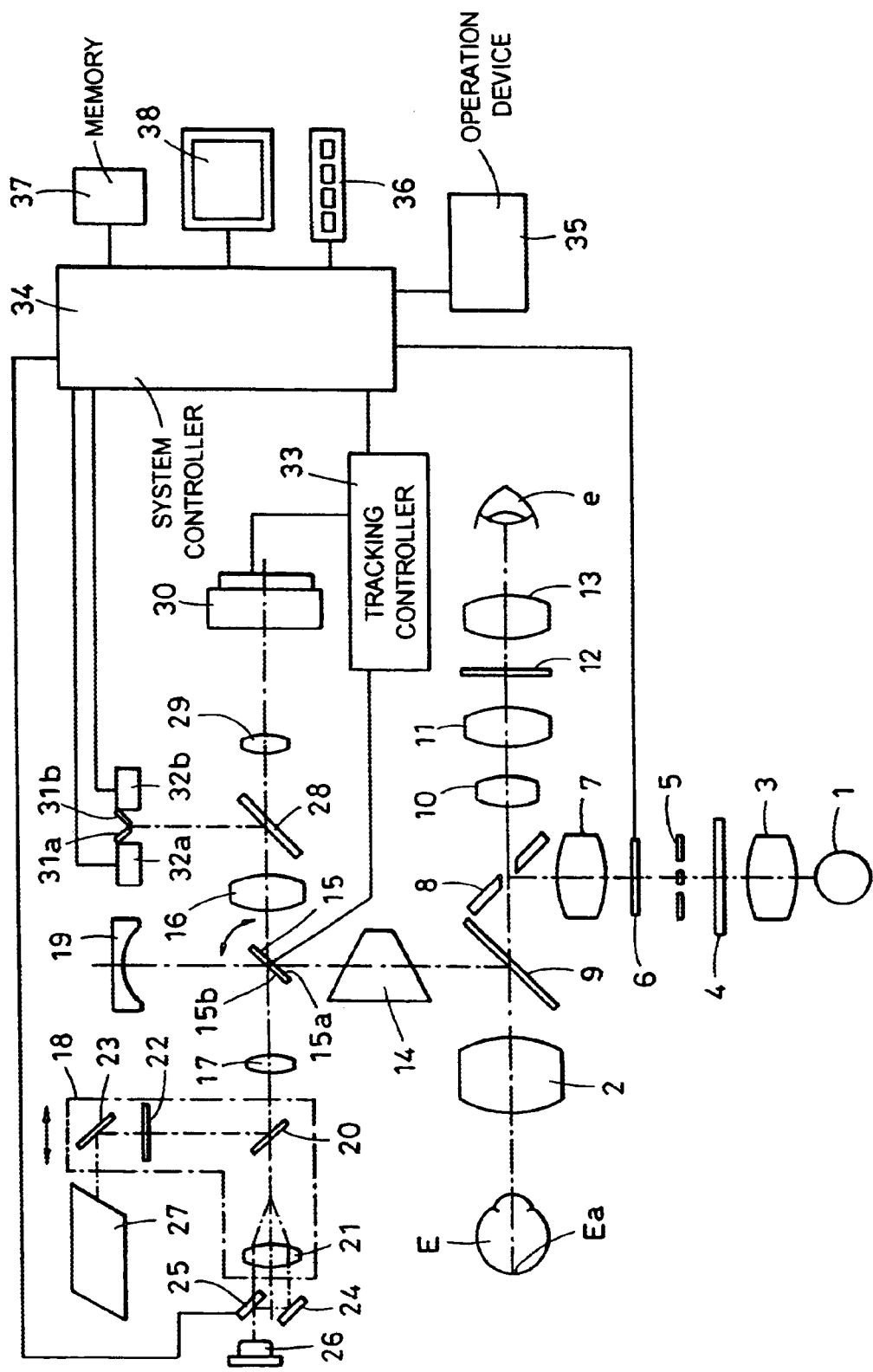
FIG. 1 is a schematic diagram illustrating an eye-fundus-blood-flow meter according to a first embodiment of the present invention.

The configuration of an eye-fundus-blood-flow meter according to a first embodiment of the present invention is shown in FIG. 1. In the first embodiment, the present invention is discussed in the context of an eye-fundus-blood-flow meter for measuring the flow rate of blood in an eye-fundus blood vessel. However, the present invention is applicable to a blood-flow meter for measuring the flow rate of blood in a blood vessel in the sclera.

In FIG. 1, on an illumination optical path from an observation light source 1 formed of a tungsten lamp, which emits white light, to an objective lens 2 which faces an eye E, a condenser lens 3, a band-pass filter 4, which transmits, for example, only yellow-range wavelength light, a ring slit 5, which is in a substantially conjugate position with the pupil of the eye E, a transmitting-type liquid crystal panel 6 for displaying a movable fixation point along the optical path, a relay lens 7, an apertured mirror 8, and a band-pass mirror 9, which transmits the yellow-range wavelength light and reflects most of the other ranges of light, are sequentially disposed. The ring slit 5 separates the eye-fundus illuminating light from the eye-fundus observation light at the front portion of the eye. Any configuration of the ring slit 5 and any number of slits can be used as long as the ring slit 5 forms a required light-shielding region.

Behind the apertured mirror 8, an observation optical system for the eye fundus is formed, comprising a focusing lens 10, which is movable along the optical path, a relay lens 11, a scale plate 12, and an eyepiece lens 13, which are sequentially disposed before an operator's eye "e".

On the optical path in the reflecting direction of the band-pass mirror 9, an image rotator 14 and a galvanometric mirror 15, having both sides polished and having a rotational axis perpendicular to the plane of the drawing, are disposed. A second focusing lens 16, movable along the optical axis, is provided in the reflecting direction of a lower reflecting surface 15a of the galvanometric mirror 15. A lens 17 and a focusing unit 18, which is movable along the optical axis, are provided in the reflecting direction of an upper reflecting surface 15b of the galvanometric mirror 15.

The front focal plane of the lens 17 is conjugate with the pupil of the eye E, and the galvanometric mirror 15, which is asymmetrically configured with respect to the pupil, is disposed at the focal plane. A concave mirror 19 is concentrically located on the optical axis behind the galvanometric mirror 15. With this arrangement, a relay optical system, which forms an image on the upper reflecting surface 15b and the lower reflecting surface 15a with -1 times magnification, is formed so that a laser beam reflected by the upper reflecting surface 15b of the galvanometric mirror 15 passes through a slit of the galvanometric mirror 15.

In the focusing unit 18, a dichroic mirror 20 and a condenser lens 21 are sequentially disposed on the same optical path as the lens 17, while a mask 22 and a mirror 23 are sequentially disposed on the optical path of the reflecting direction of the dichroic mirror 20. The focusing unit 18 is integrally movable in the directions indicated by the double-sided arrow.

On the optical path in the direction of incidence of the condenser lens 21, a stationary mirror 24 and an optical-path switching mirror 25, which is retractable from the optical path, are located in parallel to each other. A measurement light source 26, such as a laser diode, is disposed on the optical path in the direction of incidence of the optical-path switching mirror 25. A tracking light source 27 for emitting high luminance light, for example, green light, different from the other types of light sources used in this blood-flow meter, is also disposed on the optical path of the direction of incidence of the mirror 23.

A dichroic mirror 28, a magnifying lens 29, and a linear CCD 30, provided with an image intensifier, are sequentially disposed behind the second focusing lens 16 on the optical path in the reflecting direction of the lower reflecting surface 15a of the galvanometric mirror 15, thereby forming a blood-vessel-detection system. Mirrors 31a and 31b, which form a received-light pupil, and photomultipliers 32a and 32b are disposed on the optical path in the reflecting direction of the dichroic mirror 28, thereby forming a measurement-light-receiving system. For ease of representation, all the optical paths are shown in the same plane. In actuality, however, the mirrors 31a and 31b and the photomultipliers 32a and 32b are located perpendicularly to the plane of the drawing.

The output of the linear CCD 30 is connected to a tracking controller 33, and an output of the tracking controller 33 is connected to the galvanometric mirror 15 and is also connected to a system controller 34, which controls the overall operation of the flow meter. The system controller 34 comprises a computer system for executing a program with a processor. The system controller 34 is connected to the liquid crystal panel 6, the optical-path switching mirror 25, the photomultipliers 32a and 32b, an operation device 35, a selection switch panel 36 on which a plurality of switches are disposed to select a certain direction from different directions for performing re-measurements, and a memory 37. The output of the system controller 34 is transmitted to a display device 38 for displaying measurement results, which is connected to the system controller 34. A plurality of re-measurement selection buttons displayed on the selection switch panel 36 form an input device for instructing re-measurement.

Figure 2:
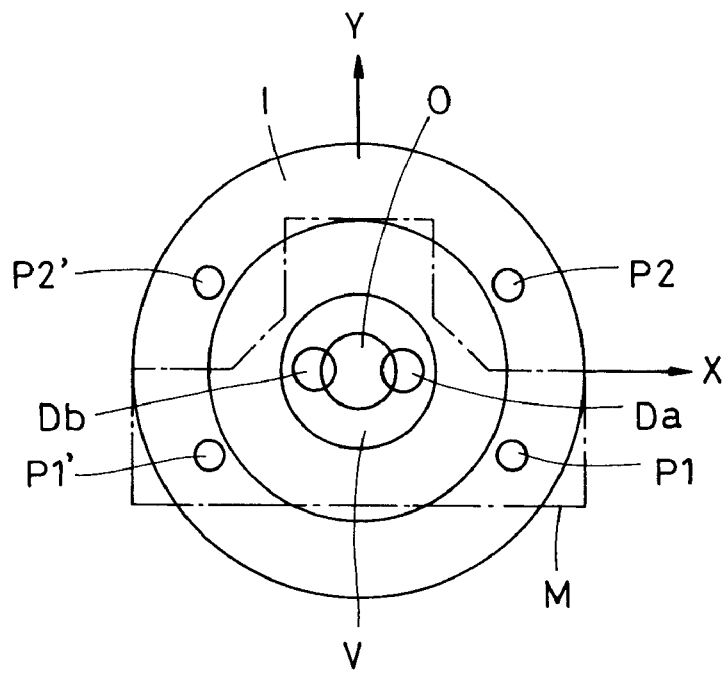
FIG. 2 illustrates the schematic arrangement of beams of light on the pupil of an eye E.

FIG. 2 illustrates the arrangement of beams of light on the pupil of the eye E. In FIG. 2, I denotes the image of the ring slit 5 in a region to which yellow-range illuminating light is applied, O denotes the position of the beam of light for observing the eye fundus and represents an image of the opening portion of the apertured mirror 8, V denotes the positions of the measuring beam/light received from the blood vessel, and represents an image of the effective portions of the upper and lower reflecting surfaces 15b and 15a, respectively, of the galvanometric mirror 15, and Da and Db denote the two received beams of light and represent images of the pair of mirrors 31a and 31b. P2 and P2' denote the positions of the measuring light selected by switching the optical-path switching mirror 25 to the position in the path from the light source 26 to the lens 21. A region M surrounded by a one-dot chain line denotes the image of the lower reflecting surface 15a of the galvanometric mirror 15. P1 and P1' denote the position of spot images of the measurement light incident on the eye fundus when the optical-path switching mirror retracts from the optical path of light from light source 26 to lens 21.

A beam of white light emitted from the observation light source 1 passes through the condenser lens 3, and the band-pass filter 4 transmits only the yellow-range wavelength light. Then, after passing through the ring slit 5, the beam of light illuminates the liquid crystal panel 6 from behind, passes through the relay lens 7, and is reflected by the apertured mirror 8. Thereafter, the band-pass mirror 9 transmits only the yellow-range wavelength light, which passes through the objective lens 2, and an image is temporarily formed as a ring slit image on the pupil of the eye E, which illuminates the eye fundus Ea almost uniformly. In this case, a fixation target is displayed on the liquid crystal panel 6. The fixation target is projected on the eye fundus Ea of the eye E by the illumination light, and is presented to the eye E as a fixation point image.

The beam of light reflected by the eye fundus Ea returns via the same optical path, and is extracted as a beam of light for observing the eye fundus. The observation beam of light then passes through the opening at the center of the apertured mirror 8, the focusing lens 10, and the relay lens 11, and an image is formed as an eye fundus image Ea' on the scale plate 12. Subsequently, the eye fundus image Ea' is observed by the operator's eye "e" via the eyepiece 13. While the eye fundus image Ea' is observed, the alignment of the blood-flow meter is performed.

When the optical-path switching mirror 25 is placed in the optical path of light from light source 26 to lens 21, the measuring beam of light emitted from the measurement light source 26 is reflected by the optical-path switching mirror 25 and the stationary mirror 24, and passes through the lower portion of the condenser lens 21 and the dichroic mirror 20 transmits the measuring beam of light. In contrast, when the optical-path switching mirror 25 retracts from the optical path, the measuring beam of light directly passes through the upper portion of the condenser lens 21, and the dichroic mirror 20 transmits the measuring beam of light.

The tracking beam of light emitted from the tracking light source 27 is reflected by the mirror 23, and is then shaped into a desired configuration by the mask 22. The tracking beam of light is then reflected by the dichroic mirror 20, and is superimposed on the measuring beam of light from the condenser lens 21, which forms a spot-like image at a conjugate position with the center of the opening of the mask 22. The superimposed measuring beam of light and the tracking beam of light pass through the lens 17, and are temporarily reflected by the upper reflecting surface 15b of the galvanometric mirror 15. The superimposed measuring beam of light and the tracking beam of light are then reflected by the upper reflecting surface 15b to the concave mirror 19, are reflected by the concave mirror 19, and return to the galvanometric mirror 15. Because of the function of the relay optical system, both beams of light reflected by the upper reflecting surface 15b of the galvanometric mirror 15 return to the position of the slit of the galvanometric mirror 15 and travel to the image rotator 14 without being reflected by the galvanometric mirror 15.

After passing through the image rotator 14, the beams of light are deflected to the objective lens 2 by the band-pass mirror 9 and irradiate the eye fundus Ea of the eye E via the objective lens 2. In this case, the tracking beam of light has been shaped by the mask 22 to a size of about 300 to 500 μm in the blood-vessel direction and about 500 to 1200 μm in a direction perpendicular to the blood vessel so that it illuminates a rectangular region to cover the vessel including the measuring point. The measuring beam of light is configured as a circular spot of about 50 to 120 μm, which is roughly equivalent to the thickness of the blood vessel to be examined, or in an elliptical shape, which is elongated in the blood-vessel direction.

The two beams of light scattered and reflected by the eye fundus Ea are again condensed by the objective lens 2, are reflected by the band-pass mirror 9, and passes through the image rotator 14. The beams of light are then reflected by the lower reflecting surface 15a of the galvanometric mirror 15, and pass through the focusing lens 16. Then, the beams of light are separated into the measuring beam of light and the tracking beam of light at the dichroic mirror 28.

The tracking beam of light then passes through the dichroic mirror 28 and forms a blood-vessel image, which is magnified at a greater scale than the eye fundus image Ea' formed by the observation optical system, on the linear CCD 30 by the magnifying lens 29. The imaging region of the linear CCD 30 is substantially the same as the illuminating range of the tracking light. The CCD 30 generates a signal, which is input into the tracking controller 33, and is converted into a blood-vessel-position signal. By using the blood-vessel-position signal, the tracking controller 33 controls the rotational angle of the galvanometric mirror 15 so as to track the blood vessel.

Part of the beams of light scattered and reflected by the eye fundus Ea in response to irradiating the eye with the measuring beam of light and the tracking beam of light passes through the band-pass mirror 9, and is guided to the observation optical system behind the apertured mirror 8. The tracking beam of light forms an image as a bar-like indicator on the scale plate 12, while the measuring beam of light forms an image as a spot image at the center of this indicator. These images are observed together with the eye fundus image and the fixation point image by the operator's eye "e" via the eyepiece lens 13. In this case, the spot image formed by the measuring beam of light is superimposed on the center of the indicator. The indicator can be linearly moved on the eye fundus Ea by rotating the galvanometric mirror 15 by using the operation device 35.

In performing the measurements, the operator first focuses the eye-fundus image. By adjusting the focus knob of the operation device 35, the liquid crystal panel 6, the focus lenses 10 and 16, and the focusing unit 18 are moved along the optical path in association with each other by a driving mechanism (not shown). When the eye fundus image is focused, the liquid crystal panel 6, the scale plate 12, and the linear CCD 30 simultaneously become conjugate with the eye fundus Ea.

After focusing the eye fundus image, the operator operates the operation device 35 to change the observation region by guiding the fixation of the eye E, and to move the subject blood vessel V to a suitable position. The system controller 34 controls the liquid crystal panel 6 to move the fixation point image. The operator also rotates the image rotator 14 so that the line connecting the centers of the photomultipliers 32a and 32b becomes parallel to the direction of the subject blood vessel V. In this case, by rotating the galvanometric mirror 15, the direction perpendicular to the arrangement of the pixels of the linear CCD 30 and the moving direction of the measuring beam are also adjusted to the direction perpendicular to the blood vessel V. After completing the adjustment of the angle, the operator actuates the operation device 35 to move the center of the indicator to a portion to be examined. The operator then actuates the operation device 35 to input a tracking start instruction.

Upon inputting the tracking start instruction into the tracking controller 33 from the operation device 35 via the system controller 34, the tracking controller 33 calculates the amount of movement of the blood vessel image from a linear reference position based on the received light from the linear CCD 30. Based on this amount of movement, the tracking controller 33 drives the galvanometric mirror 15 so that the position of the blood vessel image on the linear CCD 30 is fixed.

After checking the quality of the tracking position by starting the tracking operation, the operator presses a measurement switch of the operation device 35 to start the measurements. Then, the optical-path switching mirror 25 is moved into the optical path by the system controller 34.

Then, the measuring beam of light incident on the pupil of the eye E as spot images P1 and P2, i.e., the beam of light from a path 1, defined as the path of measuring light from measuring light source 26 to eye E when optical-path switching mirror 25 is placed in the optical path from measuring light source 26 to lens 21, and scattered and reflected by the eye fundus Ea is received by the photomultipliers 32a and 32b. The photomultipliers 32a and 32b then generate a signal that is input into the system controller 34 and is measured for, for example, two seconds. During the measurements, the measuring beam is held on the blood vessel by the function of the tracking controller 33.

Figure 3:
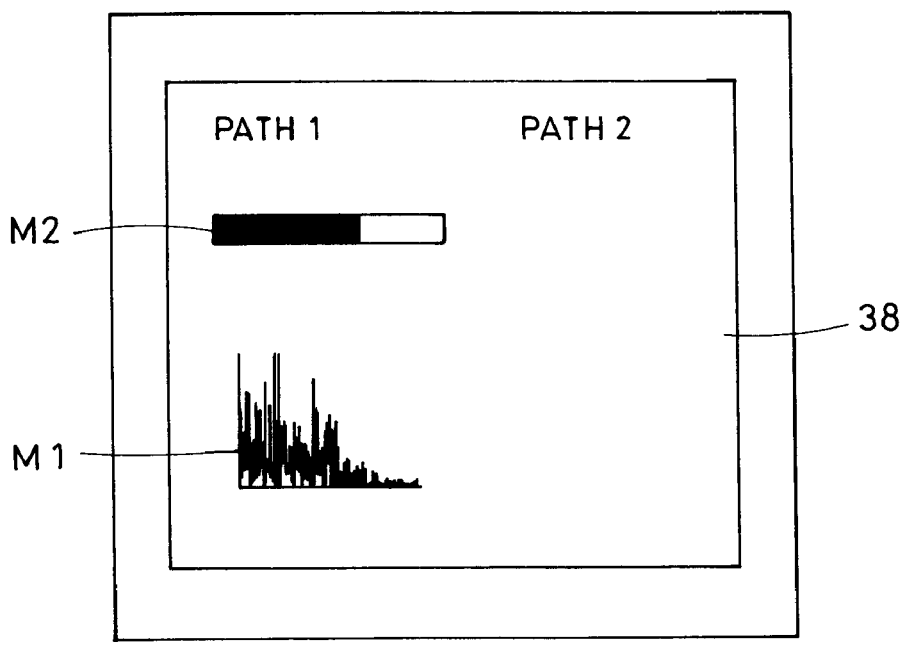
FIG. 3 illustrates the screen of a display device while a measurement operation is performed.

The system controller 34 performs fast Fourier transform (FFT) processing on the signal generated by the photomultiplier 32a at intervals of 20 ms, and the resulting FFT waveform is displayed on the display device 38 simultaneously with receiving of the signal. The horizontal axis in this graph is time and the vertical axis represents the values of the power spectrum. FIG. 3 illustrates an example of what is displayed on the screen of the display device 38, i.e., an FFT waveform M1 is shown. As the FFT waveform M1 become closer to the ideal rectangular waveform, a better measuring condition is obtained. Under poor tracking conditions in which the measuring beam is not applied to the center of the blood vessel, or under poor measuring conditions, such as the patient blinking, or the eclipse of the measuring beam of light by the patient's eyelashes, the FFT waveform M1 becomes farther away from the ideal rectangular waveform.

The system controller 34 also calculates an evaluation value indicating the quality of the received-light signal generated by photomultipliers 32a and 32b, i.e., the quality of the FFT waveform, from the FFT waveform M1, and displays a bar M2, which becomes longer or shorter according to the evaluation value, on the display device 38. In this embodiment, the bar M2 becomes longer as the quality of the received-light signal improves, which enables the operator to easily determine the quality of the signal generated by the photomultipliers 32a and 32b. In this embodiment, since the two photomultipliers 32a and 32b are different merely in the receiving directions with respect to a portion of the eye to be examined, the received-light signal only from the photomultiplier 32a is used to provide a simple representation. However, both the photomultipliers 32a and 32b may be used, in which case, the average of the evaluation values from both the photomultipliers 32a and 32b may be calculated to determine the quality of the received light signal with higher precision.

Figure 4:
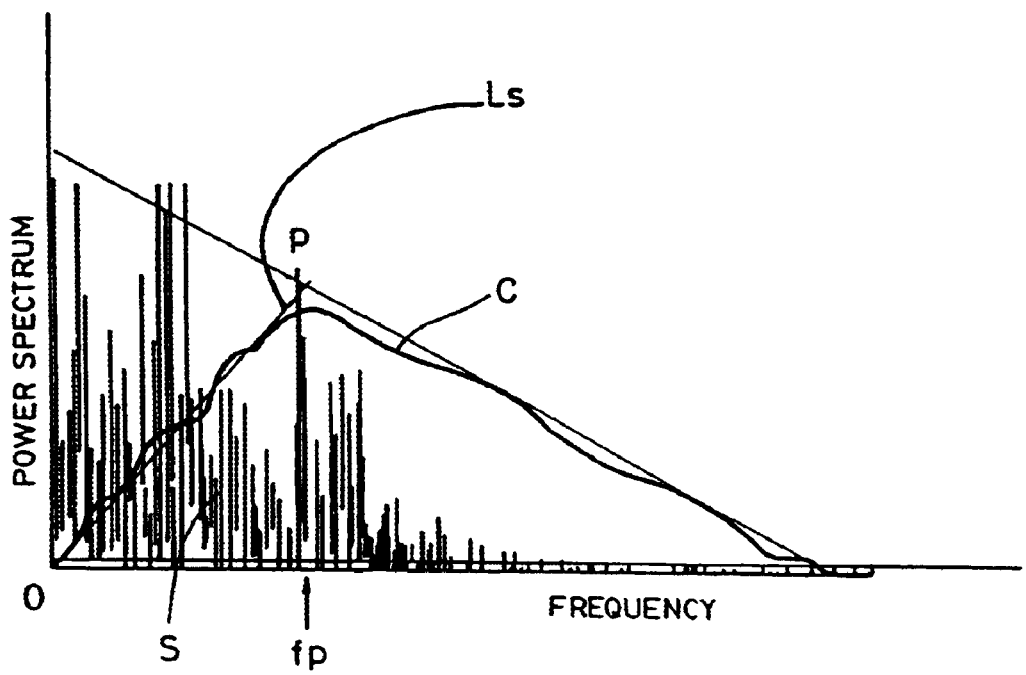
FIG. 4 illustrates a graph of a technique for obtaining an evaluation value indicating the quality of a signal.

FIG. 4 illustrates a graph from which the evaluation value can be obtained. S represents an example of the FFT waveform. From the straight line connecting the start point and the end point of the curve obtained by integrating the FFT waveform S from higher to lower frequencies, the value of the curve at corresponding points is subtracted to obtain the curve C. Ls is a straight line obtained by linearly approximating the curve C at a frequency lower than the frequency where the curve C peaks, denoted by "p". If the size of the received-light pupil is not considered, the configuration of the ideally obtained FFT waveform is a rectangle, and a portion of the curve C corresponding to a frequency range from 0 to fp becomes straight. Accordingly, the difference between the approximated straight line Ls and the actual curve epo is calculated in the frequency range from 0 to fp. This difference is called the calculated residual. The difference between the calculated residual and a predetermined constant value is determined to be the evaluation value. When the evaluation value is calculated in this way, the quality of the received-light signal is higher with a larger evaluation value.

Figure 5:
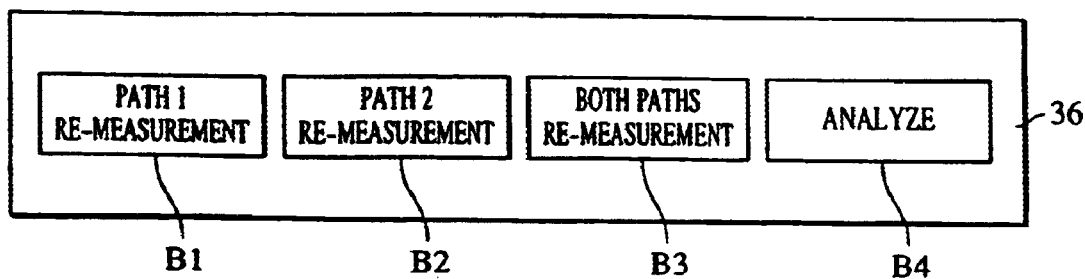
FIG. 5 is a schematic front view illustrating a selection switch panel.

FIG. 5 illustrates details of the selection switch panel 36. Among four buttons, i.e., a "path 1 re-measurement" button B1, a "path 2 re-measurement" button B2, a "both paths re-measurement" button B3, and an "analyze" button B4, one of the buttons B1, B2, and B3, which form an input device, is selected to give a re-measurement instruction. When the operator determines that the measurement condition of the path 1 is obviously unsatisfactory by checking the information of the measurement condition on the display device 38 during the measurement operation, he/she presses the "path 1 re-measurement" button B1 on the selection switch panel 36 to re-adjust the alignment, and checks the fixation state or the eyelid opening state of the patient. Then, the operator performs the re-measurement of the path 1.

In this embodiment, the FFT waveform M1 obtained by processing the received-light signal and the bar M2 indicating the evaluation value are displayed on the display device 38. However, sound output devices, such as a speaker, a headphone, and an earphone, may be provided to convert the received-light signal into sound, and the operator may determine the quality of the received-light signal from the sound. In this case, it can be determined that the quality of the received-light signal is higher with a clearer sound. This saves the operator from observing the display device 38 while performing measurements and enables him/her to concentrate on the patient.

As stated above, while performing measurement of the path 1, the tracking controller 33 calculates the amount of movement of the blood-vessel image from the linear reference position based on the received-light signal generated by the linear CCD 30, and stores the calculated amount in the memory 37. Immediately after the measurement, the system controller 34 displays a variation in the amount of movement over time on the display device 38. An example of a variation in the amount of movement over time is indicated by M3 in FIG. 6. In this display for waveform M3 representing the amount of blood-vessel movement over time, the horizontal axis represents time and the vertical axis represents the amount of movement of the blood vessel. As a result, the closer the graph M3 is to the horizontal axis, the less the blood-vessel movement, since the zero point of the vertical axis represents no movement. As the amount of movement of the blood vessel, M3, becomes closer to zero during the measurement, the movement of the galvanometric mirror 15 becomes smaller. In other words, the movement of the eye is smaller, and the measuring beam is constantly applied to the subject blood vessel. When the amount of movement M3 drops almost to zero immediately after it momentarily soars, it can also be established that the tracking operation has been properly performed. In this manner, the variation of the amount of movement M3 of the blood-vessel image from the linear reference position over time serves as tracking information indicating whether the tracking operation on the eye movement has been correctly performed.

Figure 6:
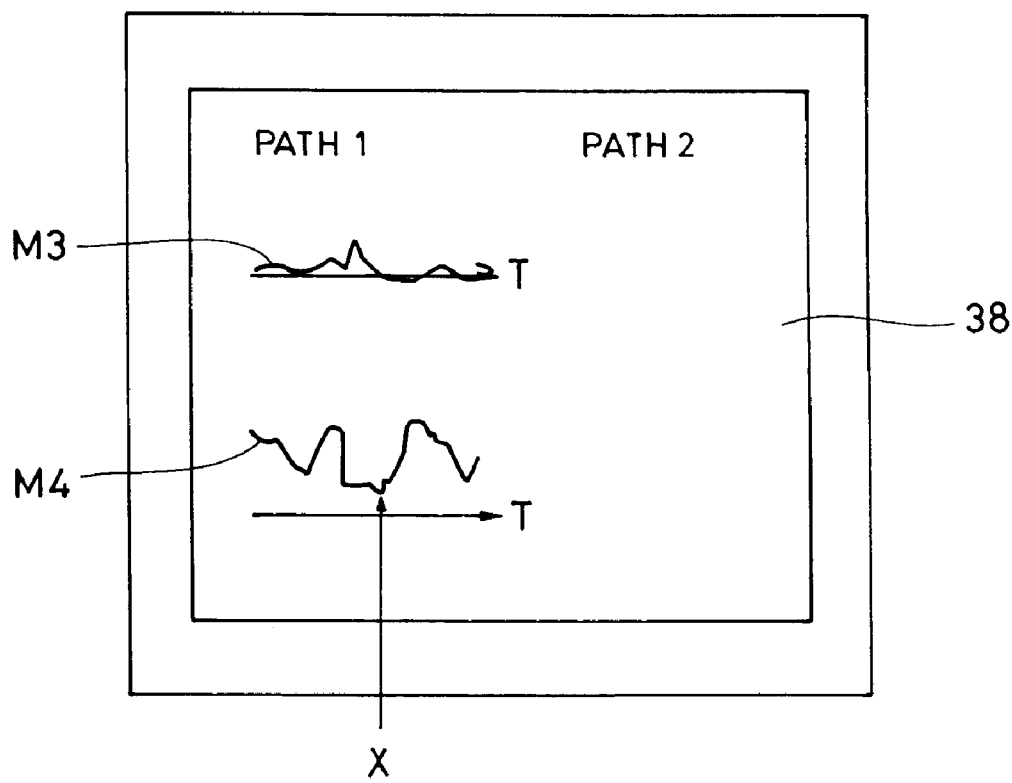
FIG. 6 illustrates the screen of the display device immediately after a measurement operation.
Figure 7:
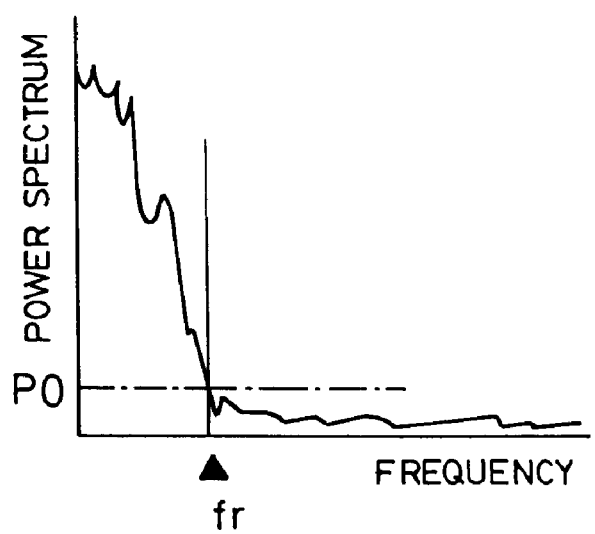
FIG. 7 illustrates a graph of a technique for obtaining a frequency fr.

Then, the received-light signal is stored in the memory 37. Subsequently, the system controller 34 performs FFT processing on the received-light signal received from the photomultiplier 32a at intervals of 20 ms so as to determine the maximum frequency fr when the power spectrum of the FFT waveform a exceeds threshold P0, as shown in FIG. 7. The frequency fr is substantially proportional to the blood-flow rate, as shown in FIG. 6, and the system controller 34 displays the variation of the frequency fr over time on the display device 38 as curve M4. The curve M4 becomes smooth under a good measurement condition. However, if the measurement condition is unsatisfactory, the variation curve M4 is disturbed as indicated by point X on the curve M4.

If the operator determines that the measurement condition of the path 1 is obviously unsatisfactory by checking the information of the measurement condition after performing the measurement, he/she presses the "path 1 re-measurement" button B1 of the selection switch panel 36 to perform the re-measurement of the path 1. The received-light signal previously stored in the memory 37 is erased before the re-measurement. Although in this embodiment the received-light signal itself is stored in the memory 37, a signal processed from the received-light signal, such as an FFT signal, may be stored instead.

Upon completion of the measurement along the path 1, the measurement along the path 2 is started. As in the measurement along the path 1, the operator inputs an instruction to start the tracking operation by using the operation device 35, and after checking that the tracking operation is properly performed, the operator presses the measurement switch of the operation device 35 to start the measurement along the path 2. Then, the optical-path switching mirror 25 retracts from the optical path from source 26 to lens 21 by the operation of the system controller 34 so as to allow the spot images P1' and P2' produced by light from source 26 traveling on path 2 to be projected from the pupil of the eye E to the subject portion of the eye E to be examined. The measurement along the path 2 is thus performed. The path 1 and the path 2 have different directions of incidence of the measuring beam of light on the subject portion of the eye. The spot images P1' and P2' on the pupil of the eye E are positioned, as shown in FIG. 2, so that the centers of the spot images P1' and P2' are located on a straight line which passes through the centers of the corresponding spot images P1 and P2 and which is parallel to a straight line connecting the centers of the measuring beams of light Da and Db.

Figure 8:
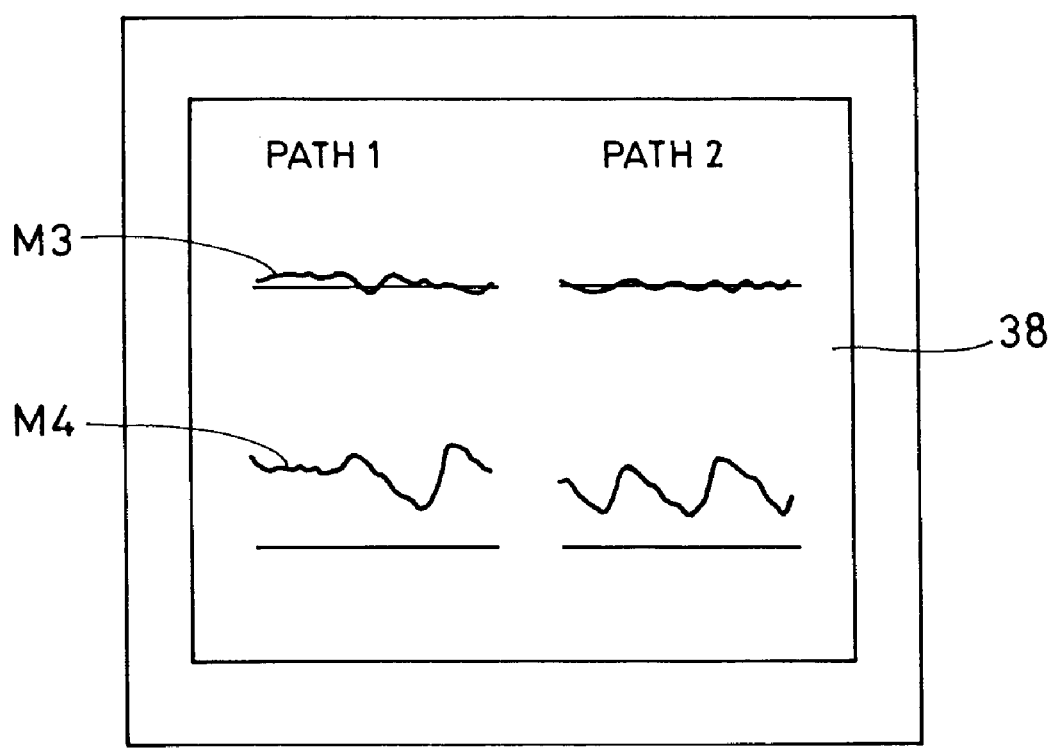
FIG. 8 illustrates the screen of the display device immediately after a measurement operation.

During the measurement along the path 2, as along path 1, the FFT waveform and a bar indicating an evaluation value are displayed at the right side of the display device 38. Immediately after the measurement, the variation of the amount of movement of the blood vessel image from the linear reference position over time and the variation of the frequency fr over time are displayed at the right side of the display device 38. FIG. 8 illustrates an example of the amount of movement and the frequency fr displayed on the display device 38 after the measurements. If the operator determines that the measurement condition along the path 2 is obviously unsatisfactory while observing the amount of movement M3 and the frequency variation curve M4, he/she immediately presses the "path 2 re-measurement" button B2 on the selection switch panel 36 so as to perform the re-measurement of the path 2.

Otherwise, the measurement information on the display device 38, i.e., the amount of movement M3 of the blood-vessel image from the linear reference position and the frequency variation curve M4 of the frequency fr obtained along the path 1, are compared with those obtained by the path 2. Upon comparison, if the result of the path 1 or that of the path 2 is unsatisfactory, the "path 1 re-measurement" button B1 or the "path 2 re-measurement" button B2 is pressed to perform the re-measurement operation. If the re-measurements of both paths are required, the "both paths re-measurement" button B3 is pressed. In performing the re-measurement, the received-light signal previously stored in the memory 37 is erased before the re-measurement operation. If the results of both paths are good, the operator presses the "analyze" button B4 to complete the measurements along both paths. Then, the system controller 34 determines the flow rate by the following analyses.

The system controller 34 first performs FFT processing on the received-light signals along the path 1 and the path 2 so as to determine the maximum frequency shifts $|\Delta f_{max1}|$ and $|\Delta f_{max2}|$ from the FFT result of the path 1 and the maximum frequency shifts $|\Delta f_{max1'}|$ and $|\Delta f_{max2'}|$ from the FFT result of the path 2. Then, the maximum blood-flow rates $V_{max}$ and $V_{max'}$ in the path 1 and the path 2, respectively, are determined from the following equations (2) and (3), which are equivalent to equation (1) by substituting 0 for $\beta$.

$$V_{max} = \{\lambda/(n\cdot\alpha)\} \cdot ||\Delta f_{max1}| - |\Delta f_{max2}|| \quad (2)$$

$$V_{max'} = \{\lambda/(n\cdot\alpha)\} \cdot ||\Delta f_{max1'}| - |\Delta f_{max2'}|| \quad (3)$$

If there is a large disparity between the value of $V_{max}$ and the value of $V_{max'}$, the larger value is determined to be the true blood-flow rate and is displayed on the display device 38. When the two values $V_{max}$ and $V_{max'}$ are roughly the same, the average thereof is displayed on the display device 38 as the true blood-flow rate. The reason for not using the smaller value of $V_{max}$ or $V_{max'}$ is to avoid the following situation. The signs of $f_{max1}$ and $f_{max2}$, or $f_{max1'}$ and $f_{max2'}$ may be different, i.e., they may be positive and negative, in which case, the maximum blood-flow rates $V_{max}$ and $V_{max'}$ may not be correctly determined by equations (2) and (3), respectively. In other words, the values $V_{max}$ and $V_{max'}$ may become far from the true maximum flow rate.

Conventionally, if the measurement of one path is not correctly performed, re-measurement has to be performed on both paths. In the present invention, however, information indicating the measurement condition is displayed on the display device 38, and the input device formed of the buttons B1 through B3 on the selection switch panel 36 is provided. With this arrangement, the data along the path obtained by the correct measurement is not wasted, and a duplicate measurement along the correctly measured path can be avoided. Thus, many portions can be examined.

Additionally, immediately after the measurements along both paths, the information of the measurement conditions along both paths, i.e., the variation in the amount of movement of the blood vessel image from the linear reference position over time and the frequency fr over time are simultaneously displayed on the display device 38. Thus, the path 1 and the path 2 can be compared with each other, thereby making it possible to easily determine whether the re-measurement is to be performed. The measurement state may be different among the portions of the eye to be examined, and it cannot always be determined to be satisfactory only by checking the measurement condition. However, the measurement condition should be almost the same between the two paths, and by comparing the two paths, the above-described problem can be solved.

Although in this embodiment a variation in the frequency fr over time is used as one type of the measurement information, other types of information related to the flow rate, such as a variation in the maximum amount of frequency shift over time or a variation in the maximum flow rate over time, may be displayed on the display device 38.

Second Embodiment

Figure 9:
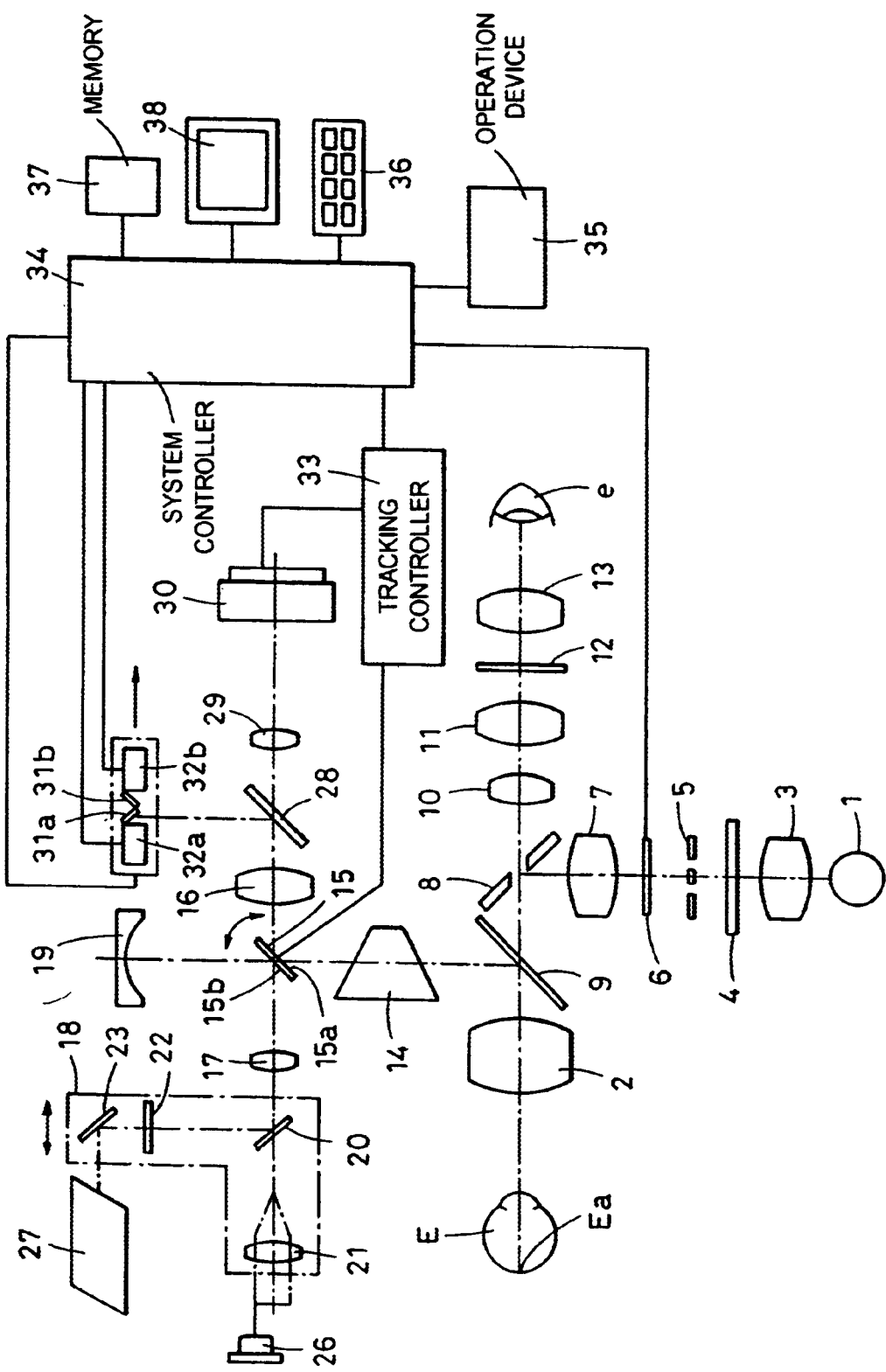
FIG. 9 is a schematic diagram illustrating an eye-fundus-blood-flow meter according to a second embodiment of the present invention.

FIG. 9 illustrates the configuration of a second embodiment. The reference numerals in FIG. 9 that are the same as in FIG. 1 denote identical elements. In the first embodiment, by inputting a beam of light from two directions, the problem of the signs of $|\Delta f_{max1}|$, $|\Delta f_{max2}|$, $|\Delta f_{max1'}|$, and $|\Delta f_{max2'}|$ is solved. In the second embodiment, the problem of the signs can be overcome by changing the received-light positions.

A beam of light from the measurement light source 26 is reflected by the eye E at the position P1' in FIG. 2 behind the image M of the galvanometric mirror 15, and returns to the position P2' located at the slit of the galvanometric mirror 15. Thus, a beam of light is incident in only one direction. The mirrors 31a and 31b and the photomultipliers 32a and 32b are integrally formed into one unit, and are movable by the system controller 34 perpendicularly to the optical system for receiving the measuring signals.

Figure 10:
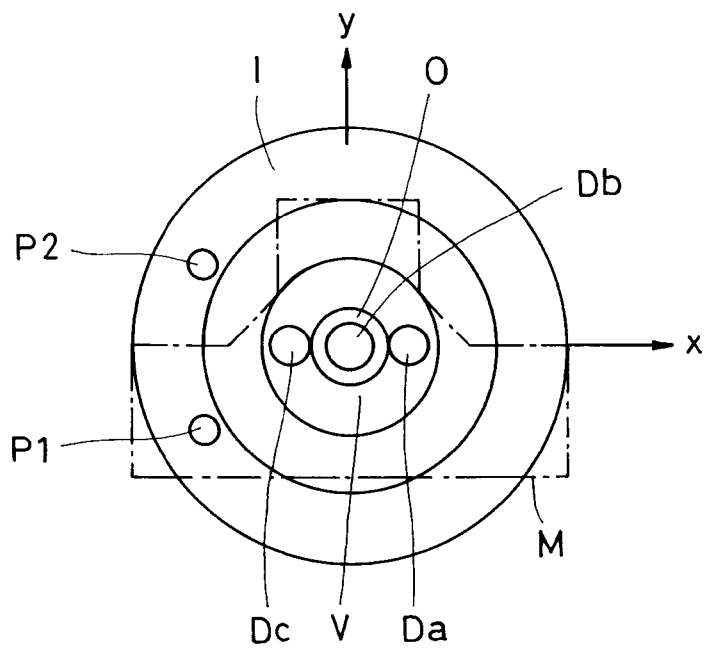
FIG. 10 illustrates a schematic arrangement of beams of light on the pupil of the eye E.

FIG. 10 illustrates the arrangement of beams of light on the pupil of the eye E, and the arrangement shown in FIG. 10 is different from the counterpart of FIG. 2 in the following respects. Dc indicates a beam of received light selected when the photomultipliers 32a and 32b are moved, and Da, Db, and Dc are aligned at the opening portion of the apertured mirror 8. In other respects, FIG. 10 is the same as FIG. 2 and reference letters in FIG. 10 that are the same as in FIG. 2 denote identical items, except as noted above.

The operation of the blood flow meter of the second embodiment is similar to that of the first embodiment. In the second embodiment, however, when the operator starts the measurement along the path 2 upon completing the correct measurement along the path 1, the system controller 34 moves the mirrors 31a and 31b and the photomultipliers 32a and 32b, which are integrally formed into one unit, as indicated by the one-dot-chain line, in the direction indicated by the double-sided arrow in FIG. 9. In this state, the photomultiplier 32a receives the beam of light Db, while the photomultiplier 32b receives the beam of light Dc.

Then, the measurement along the path 2 is started, and upon completing the correct measurement along the path 2, the system controller 34 calculates $|\Delta f_{max1}|$ and $|\Delta f_{max2}|$, $|\Delta f_{max1'}|$ and $|\Delta f_{max2'}|$, and the maximum blood-flow rates $V_{max}$ and $V_{max'}$, from the received-light signals stored in the memory 37, as in the first embodiment.

In the second embodiment, the system controller 34 calculates an evaluation value, as discussed in the first embodiment, at intervals of 20 ms for the received-light signal generated by the photomultiplier 32a in response to measurement light reflected by the eye falling on CCD 30 and stored in the memory 37, and displays the variation in the evaluation value over time on the display device 38 immediately after the measurement along each path.

Figure 11:
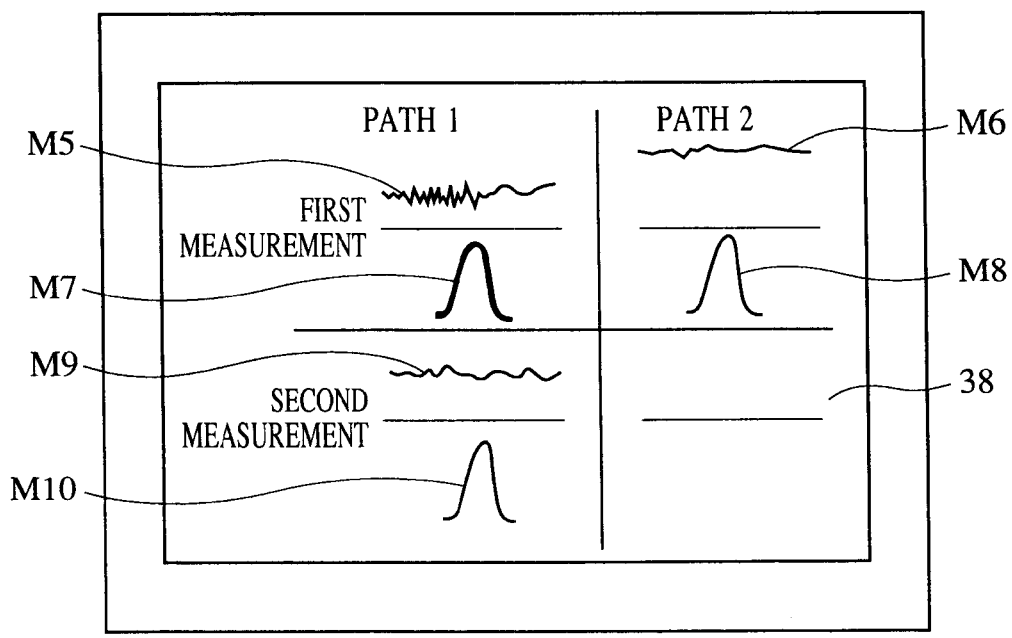
FIG. 11 illustrates the screen of the display device immediately after a measurement operation.

M5 and M6 in FIG. 11 respectively indicate examples of the variation in the evaluation value calculated from light traveling along the path 1 and the path 2 over time. The quality of the signal is higher with a larger evaluation value. Accordingly, a comparison of the evaluation value calculated from light traveling along the path 1 and the path 2 and a determination of the need to re-measure can easily be performed.

The system controller 34 also calculates the vessel size based on the blood-vessel images incident on the linear CCD 30, and thirty blood-vessel images are captured while measurements are performed for two seconds. The system controller 34 then displays the thirty blood-vessel images by overlapping them on the display device 38 immediately after the measurement along each path.

The overlapped blood vessel images generated by measuring light traveling along the path 1 and the path 2 are indicated by M7 and M8, respectively, in FIG. 11. In the case of a poor tracking operation, the blood-vessel images are displaced from each other, and the overlapped images appear to be one thick line, as indicated by M7. The overlapped blood-vessel images indicated by M8 reveal that the tracking operation has been properly performed. The blood-vessel images are disturbed not only by a poor tracking operation, but also by eyelashes or tears. The second embodiment can handle a greater variety of poor measurement states than the first embodiment, in which the amount of movement of the blood-vessel image from the linear reference position is displayed. Instead of displaying the blood-vessel images, a variation in the calculated vessel sizes may be displayed, thereby more easily determining the quality of the measurement state.

Figure 12:
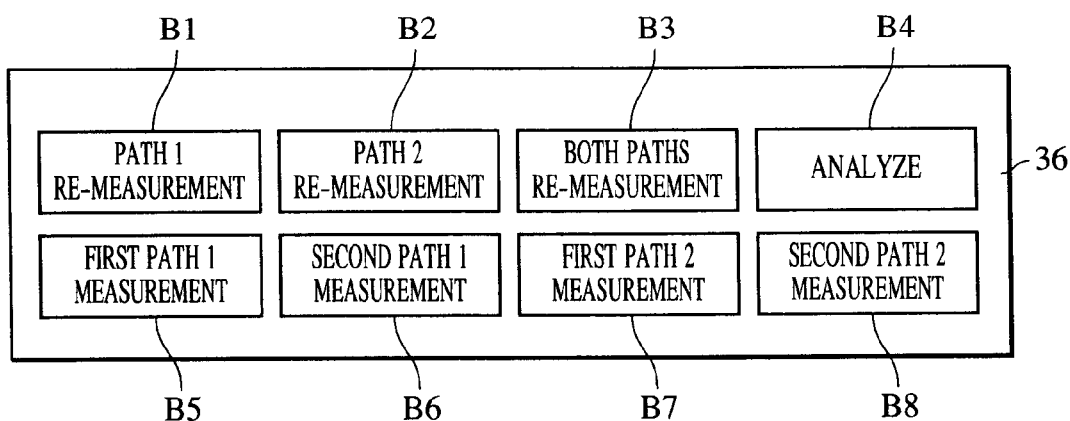
FIG. 12 is a schematic front view illustrating the selection switch panel.

FIG. 12 illustrates details of the selection switch panel 36. Buttons B1 through B4 are similar to those of the first embodiment. In addition to the buttons B1 through B4, a selector formed of a "first path 1 measurement" button B5, a "second path 1 measurement" button B6, a "first path 2 measurement" button B7, and a "second path 2 measurement" button B8 is formed for selecting the selection result. As in the first embodiment, the operator compares the measurement condition along the path 1 with that along the path 2 so as to determine whether the re-measurement is required. According to the determination, one of the buttons B1 through B4 is selected. When the re-measurement is performed, the variation in the evaluation value over time and the overlapped blood-vessel images, which serve as information of the first measurement state before the re-measurement, are displayed on the upper portion of the display device 38, and the information of the second measurement state after the re-measurement is displayed on the lower portion of the display device 38.

M9 and M10 in FIG. 11 respectively indicate examples of the variation in the evaluation value over time and the overlapped blood-vessel images, when the re-measurement of the path 1 is performed. The operator compares the measurement condition of the path 1 with that of the path 2. The operator also compares the first measurement condition before the re-measurement and the second measurement condition after the re-measurement, and selects the better measurement result by pressing one of the buttons B5 through B8. In this example, the re-measurement is performed on only the path 1, and if, for example, the second measurement condition is selected, the "second path 1 measurement" button B6 is pressed. The system controller 34 then analyzes the selected result to determine the blood-flow rate, as in the first embodiment.

According to the above description, in the second embodiment, the measurement result associated with the path 1 is compared with that associated with the path 2, and also, the first measurement condition and the second measurement condition before and after the re-measurement are compared. Accordingly, the better result can be used. Thus, if the first measurement result is better than the second measurement result, it can be effectively used without being wasted. The measurement precision can also be improved.

In this embodiment, the re-measurement is performed only once. However, more re-measurements may be performed, in which case, the measurement conditions may be compared, and the best result can be selected.

When the position of the received-light pupil is moved as in the second embodiment, only the beam of light Dc may be measured when the measurement along the path 2 is performed. In this case, concerning the measurement of the beam of light Db, the measurement result along the path 1 may be used. Additionally, three photomultipliers may be prepared for the beams of light Da, Db, and Dc so as to deflect the beams in different directions in the light-receiving system, thereby changing the measuring direction.

Third Embodiment

Figure 13A:
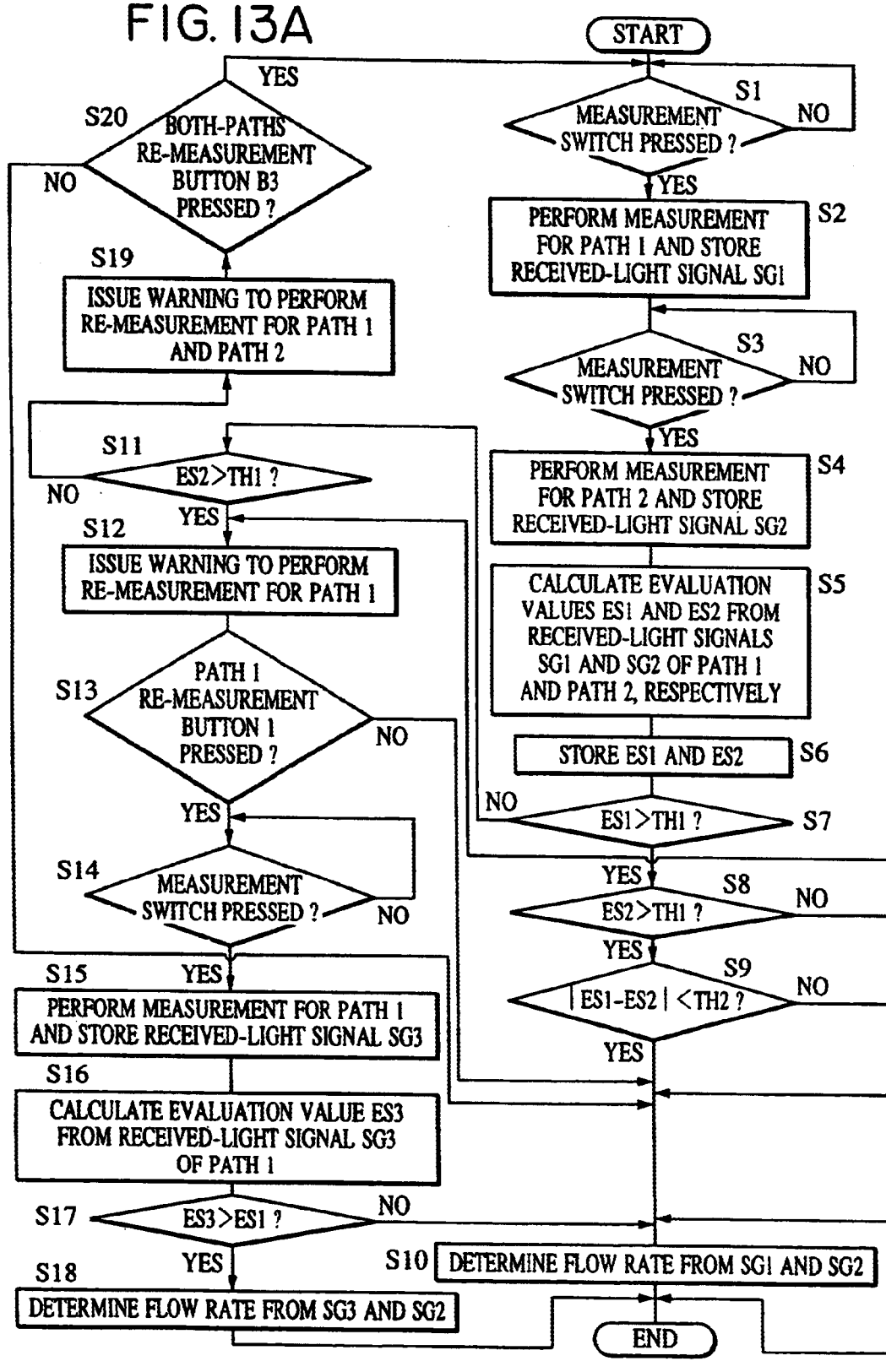

FIGS. 13A and 13B are a flow chart illustrating a third embodiment. The overall configuration of the blood-flow meter of the third embodiment is similar to that of the first embodiment shown in FIG. 1. However, the operation of the re-measurement performed by the system controller 34 is different from that of the first embodiment. In the third embodiment, it is automatically determined by the blood flow meter whether the re-measurement is required, and the determination result is displayed, and more specifically, if the re-measurement is required, a warning is issued.

In step S1, the system controller 34 determines whether the measurement switch of the operation device 35 is pressed. If the measurement switch is not pressed, step 1 is repeated, i.e., the system controller 34 waits for an input from the measurement switch. When the measurement switch is pressed, the process proceeds to step S2 in which the system controller 34 advances the optical-path switching mirror 25 into the optical path from source 26 to lens 21, and records received-light signals of the photomultipliers 32a and 32b for two seconds. That is, the measurement of measuring light traveling along the path 1 and reflected by eye E is performed, and a received-light signal SG1 generated by photomultipliers 32a and 32b is stored in the memory 37. The system controller 34 then determines in step S3 whether the measurement switch is pressed. If the result of step S3 is no, step S3 is repeated, i.e., the system controller 34 waits for an input from the measurement switch. When the measurement switch is pressed, the process proceeds to step S4 in which the system controller 34 retracts the optical-path switching mirror 25 from the optical path of light from source 26 to lens 21. Then, the system controller 34 performs the measurement of measuring light traveling along the path 2 and reflected by the eye E and stores a received-light signal SG2 generated by the photomultipliers 32a and 32b in the memory 37, as in step S2.

Subsequently, in step S5, the system controller 34 calculates evaluation values ES1 and ES2 from the received-light signals SG1 and SG2, respectively, stored in the memory 37 according to a technique similar to the first embodiment. Then, in step S6, the system controller 34 stores the calculated evaluation values ES1 and ES2 in the memory 37. The system controller 34 then determines in step S7 whether the evaluation value ES1 for the path 1 is greater than a reference value TH1, that is, whether it is necessary to perform the re-measurement. If the outcome of step S7 is yes, the process proceeds to step S8, where the system controller 34 determines whether the evaluation value ES2 for the path 2 is greater than a reference value TH2. If the result of step S8 is yes, the process proceeds to step S9. In step S9, the system controller 34 determines whether the difference between the two evaluation values ES1 and ES2 is smaller than the reference value TH2. If the outcome of step S9 is yes, the process proceeds to step S10 which the system controller 34 determines the blood-flow rate from the received-light signals SG1 and SG2 stored in the memory 37.

If the system controller 34 finds in step S7 that the evaluation value ES1 for the path 1 is equal to or smaller than the reference value TH1, the process proceeds to step S11 in which the system controller 34 determines whether the evaluation value ES2 for the path 2 is greater than the reference value TH1. If the result of step S11 is yes, the process proceeds to step S12 in which the system controller 34 displays a warning message to perform the re-measurement for the path 1 on the display device 38. The system controller 34 then determines in step S13 whether the "path 1 re-measurement" button B1 of the selection switch panel 36 is pressed during a predetermined period. If the outcome of step S13 is no, the process returns to step S10 in which the system controller 34 determines the blood-flow rate from the received-light signals SG1 and SG2 stored in the memory 37.

If the system controller 34 determines that the button B1 is pressed, the system controller 34 determines in step S14 whether the measurement switch of the operation device 35 is pressed. If the result of step S14 is no, step S14 is repeated, that is, the system controller 34 waits for an input from the measurement switch. When the measurement switch is pressed, the flow proceeds to step S15. In step S15, the measurement using light traveling along the path 1 is performed, as in step S2, and the system controller 34 stores a received-light signal SG3 in the memory 37.

Thereafter, in step S16, the system controller 34 calculates an evaluation value ES3 from the received-light signal SG3 stored in the memory 37. The system controller 34 then determines in step S17 whether ES3 is greater than ES1 stored in the memory 37. If the outcome of step S17 is yes, the process proceeds to step S18 in which the system controller 34 determines the blood-flow rate from the received-light signals SG3 and SG2 stored in the memory 37. If the result of step S17 is no, the process returns to step S10 in which the system controller 34 determines the blood-flow rate from the received-light signals SG1 and SG2 stored in the memory 37.

If the system controller 34 finds in step S11 that the evaluation value ES2 for the path 2 is equal to or smaller than the reference value TH1, the process proceeds to step S19 in which the system controller 34 displays a warning message to perform the re-measurements for both path 1 and path 2 on the display device 38. Then, in step S20, the system controller 34 determines whether the "both paths re-measurement" button B3 of the selection switch panel 36 is pressed during a predetermined period. If the button B3 is pressed, the process returns to step S1. If the button B3 is not pressed, the process returns to step S10 in which the system controller 34 determines the blood-flow rate from the received-light signals SG1 and SG2.

If the system controller 34 finds in step S9 that the difference between the evaluation value ES1 for the path 1 and the evaluation value ES2 for the path 2 is equal to or greater than the reference value TH2, the process proceeds to step S21 in which the system controller 34 determines whether ES2 is greater than ES1. If the outcome of step S21 is yes, the process returns to step S12. If the result of step S21 is no, the process proceeds to step S22 in which the system controller 34 displays a warning message to perform the re-measurement for the path 2 on the display device 38. The system controller 34 then determines in step S23 whether the "path 2 re-measurement" button B2 of the selection switch panel 36 is pressed during a predetermined period. If the button B2 is pressed, the process proceeds to step S24 in which the system controller 34 determines whether the measurement switch of the operation device 35 is pressed. If not, step S24 is repeated, i.e., the system controller 34 waits for an input from the measurement switch.

When the system controller 34 determines that the measurement switch is pressed, the process proceeds to step S25. In step S25, the system controller 34 performs the measurement using light traveling along the path 2, as in step S4, and stores a received-light signal SG4 in the memory 37. Subsequently, in step S26, the system controller 34 calculates an evaluation value ES4 from the received-light signal SG4 stored in the memory 37. The system controller 34 then determines in step S27 whether ES4 is greater than ES2 stored in the memory 37. If the outcome of step S27 is yes, the process proceeds to step S28 in which the system controller 34 determines the blood-flow rate from the received-light signals SG1 and SG4 stored in the memory 37. If the result of step S27 is no, the process returns to step S10 in which the system controller 34 determines the blood-flow rate from the received-light signals SG1 and SG2 stored in the memory 37. If it is found in step S8 that the evaluation value ES2 for the path 2 is equal to or smaller than the reference value TH1, the process proceeds to step S22.

As discussed above, in the third embodiment, it is automatically determined whether the re-measurement is required, and if the re-measurement is necessary, a warning message is displayed. Thus, even an inexperienced operator is able to easily perform good measurements.

In the third embodiment, a determination is made whether it is necessary to perform the re-measurement upon completion of the measurements for the path 1 and the path 2. However, if it is obvious from the measurement result for the path 1 that the re-measurement is necessary, a warning message may be given. Additionally, although in this embodiment the display device 38 is used for displaying a warning message, other types of devices, such as a visual output device, for example, an indicator formed of a special lamp, or an audio output device may be used for emitting light or sound.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An ocular blood-flow meter comprising:
    an optical system configured and positioned to apply measuring light to a blood vessel of a subject eye, and to receive light scattered by the blood vessel of the subject eye;
    a mechanism configured and positioned to change the direction in which the measuring light is applied to the blood vessel or the direction in which the scattered light is received by at least a portion of said optical system so as to enable a plurality of measurements of the blood flow in the blood vessel using measuring light applied to the blood vessel in different directions or using scattered light received by at least a portion of said optical system in different directions;
    a device configured and positioned to receive the scattered light from said optical system,
        wherein said device outputs a received-light signal containing information on blood flow in the blood vessel in response to receiving the scattered light from said optical system;
    a controller connected to said device to receive the received-light signal and configured to perform the plurality of measurements of the blood flow in the blood vessel using the received-light signal generated from measuring light being applied to the blood vessel in different directions and scattered by the blood vessel or generated from the scattered light received by at least a portion of said optical system in different directions, wherein said controller is also configured to perform a re-measurement operation to re-measure the blood flow in the blood vessel using a received-light signal generated from measuring light being applied to the blood vessel or generated from the scattered light received by at least a portion of said optical system in a desired direction in response to an instruction by an operator to perform a re-measurement operation in the desired direction; and an input device,
wherein said input device is electrically coupled to said controller,
wherein said input device is configured to enable an operator to select a re-measurement operation to re-measure the blood flow in the blood vessel using a received-light signal generated from measuring light being applied to the blood vessel in a desired direction and then scattered by the blood vessel or generated from the scattered light received by at least a portion of said optical system in a desired direction,
wherein said input device also is configured to instruct said controller to perform the selected re-measurement operation selected by the operator.

2. An ocular blood-flow meter according to claim 1, wherein said input device comprises a selector,
wherein said selector is configured to enable the operator to select a desired measurement result from a plurality of measurement results obtained in the desired direction in which the re-measurement operation is performed.

3. An ocular blood-flow meter according to claim 1, further comprising:
a tracking system configured to track movement of the subject eye; and
a display device connected to said tracking system and configured to display tracking information obtained by said tracking system.

4. An ocular blood-flow meter according to claim 1, further comprising:
a measurement system configured to measure blood vessel size; and
a display device connected to said measurement system and configured to display the measurement result obtained by said measurement system,
wherein said measurement system is connected to said device.

5. An ocular blood-flow meter according to claim 1, further comprising a display device connected to said controller,
said display device presenting to the operator a plurality of measurement results using the received light signal output from said device so as to provide information to the operator to enable the operator to determine whether the re-measurement operation is required.

6. The ocular blood-flow meter according to claim 1, wherein said optical system comprises:
a measuring light source; and
a lens,
wherein said mechanism is positioned between said measuring light source and said lens and comprises:
a retractable optical path switching mirror; and
a stationary mirror, and
wherein said optical path switching mirror is retractable out of and insertable into the path of measuring light from said measuring light source and said lens, wherein when said optical path switching mirror is in the optical path from said measuring light source to said lens, said optical path switching mirror reflects measuring light from said measuring light source to said stationary mirror, which reflects the measuring light to a first portion of said lens, and wherein when said optical path switching mirror is out of the optical path from said measuring light source to said lens, measuring light from said measuring light source is projected directly to a second portion of said lens, whereby said mechanism changes the direction in which the measuring light is applied to the blood vessel.

7. The ocular blood-flow meter according to claim 1, wherein said mechanism changes the position of said device so as to change the direction in which the scattered light is received by at least a portion of said optical system.

8. The ocular blood-flow meter according to claim 1,
wherein said input device comprises a selection switch panel on which first, second, and third switches are disposed to select only a first direction, only a second direction, and both said first and second directions, respectively, in which the operator desires the measuring light to be applied to the blood vessel and then scattered by the blood vessel or to select only a first direction, only a second direction, and both said first and second directions, respectively, in which the operator desires that the scattered light be received by at least a portion of said optical system.

9. The ocular blood-flow meter according to claim 1, further comprising:
a tracking system configured to track movement of the subject eye,
wherein said tracking system is configured to produce a blood-vessel image of the blood vessel and a signal representing the blood-vessel image,
wherein said tracking system is connected to said controller,
wherein said controller determines the position and amount of movement of the blood-vessel image from the signal produced by said tracking system,
wherein the amount of movement of the blood-vessel image that is determined by said controller is indicative of the quality of the tracking performed by said tracking system; and
a display device connected to said tracking system and said controller;
wherein said controller processes the received-light signal over time and determines an evaluation value over time that represents the quality of the received-light signal,
wherein said controller calculates the variation in the frequency of over time of the processed received-light signal,
wherein said display device displays a first graph of the processed received-light signal over time processed by said controller,
wherein said display device displays a second graph of the evaluation value determined by said controller before and during measurement of the blood flow in the blood vessel,
wherein said display device displays a third graph representing the variation over time in the amount of movement of the blood-vessel image during measurement of the blood flow in the blood vessel, and
wherein said display device displays a fourth graph representing the variation in the frequency of over time of the processed received-light signal after measurement of the blood flow in the blood vessel.

10. The ocular blood-flow meter according to claim 9,
wherein said controller processes the received-light signal over time by performing a fast Fourier Transform operation on the received-light signal to produce a fast Fourier Transform waveform over time,
wherein said display device displays the fast Fourier Transform waveform over time as the first graph,
wherein said controller determines the maximum frequency when the power spectrum of the fast Fourier Transform waveform exceeds a predetermined threshold, and
wherein said display device displays the variation in the frequency over time of the power spectrum of the fast Fourier Transform waveform as the fourth graph.

11. The ocular blood-flow meter according to claim 1, further comprising:
an image forming system forming a blood-vessel image,
wherein said controller is configured to determine variations in the amount of movement over time of the blood-vessel image,
wherein said controller is also configured to process the received-light signal to produce a processed received-light signal and determine the frequency over time of the processed received-light signal, and
wherein said meter further comprises a display device connected to said controller,
wherein said display device displays the variations in the amount of movement over time of the blood-vessel image, and
wherein said display device displays the frequency over time of the processed received-light signal.

12. The ocular blood-flow meter according to claim 1,
wherein said controller determines an evaluation value over time that represents the quality of the received-light signal generated from measuring light being applied to the blood vessel in a first direction and scattered by the blood vessel or generated from the scattered light received by at least a portion of said optical system in a first direction,
wherein said controller determines an evaluation value over time that represents the quality of the received-light signal generated from measuring light being applied to the blood vessel in a second direction and scattered by the blood vessel or generated from the scattered light received by at least a portion of said optical system in a second direction,
wherein said meter further comprises a display device, connected to said controller,
wherein said display device displays the evaluation values over time associated with the first and second directions, simultaneously.

13. The ocular blood-flow meter according to claim 12, further comprising
an image forming system forming a blood vessel image,
wherein said meter captures the blood vessel image at different time during the plurality of measurements of the blood flow to produce a plurality of blood-vessel images of the same blood vessel over time,
wherein said meter further comprises a tracking system comprising at least one optical element tracking the blood vessel during movement of the blood vessel so that the blood vessel image of the blood vessel formed by said image forming system is positioned at substantially the same position over time during the plurality of measurements and during a re-measurement operation when tracking is properly performed,
wherein when tracking by said tracking system is not properly performed, the position of the blood-vessel image changes over time,
wherein said display device displays in an overlapping manner the plurality of captured blood-vessel images while receiving the light generated from measuring light being applied to the blood vessel in the first direction and scattered by the blood vessel or generated from the scattered light received by at least a portion of said optical system in the first direction,
wherein the thickness of the displayed, overlapped blood-vessel images associated with the first direction is greater when said tracking system performs tracking improperly than when said tracking system performs tracking properly,
wherein said display device displays in an overlapping manner the plurality of captured blood-vessel images while receiving the light generated from measuring light being applied to the blood vessel in the second direction and scattered by the blood vessel or generated from the scattered light received by at least a portion of said optical system in the second direction, and
wherein the thickness of the displayed, overlapped blood-vessel images associated with the second direction is greater when said tracking system performs tracking improperly than when said tracking system performs tracking properly.

14. The ocular blood-flow meter according to claim 13,
wherein a measurement operation performed using a received-light signal generated from measuring light being applied to the blood vessel in the first direction and scattered by the blood vessel or generated from the scattered light received by at least a portion of said optical system in the first direction is denoted as the first path 1 measurement,
wherein a re-measurement operation performed using a received-light signal generated from measuring light being applied to the blood vessel in the first direction and scattered by the blood vessel or generated from the scattered light received by at least a portion of said optical system in the first direction is denoted as the second path 1 measurement,
wherein a measurement operation performed using a received-light signal generated from measuring light being applied to the blood vessel in the second direction and scattered by the blood vessel or generated from the scattered light received by at least a portion of said optical system in the second direction is denoted as the first path 2 measurement,
wherein a re-measurement operation performed using a received-light signal generated from measuring light being applied to the blood vessel in the second direction and scattered by the blood vessel or generated from the scattered light received by at least a portion of said optical system in the second direction is denoted as the second path 2 measurement,
wherein said input device comprises:
a first selector switch permitting the operator to instruct said meter to perform a second path 1 measurement;
a second selector switch permitting the operator to instruct said meter to perform a second path 2 measurement;
a third selector switch permitting the operator to instruct said meter to perform a re-measurement operation using a received-light signal generated from measuring light being applied to the blood vessel in the first and second directions and scattered by the blood vessel or generated from the scattered light received by at least a portion of said optical system in the first and second directions;

a fourth selector switch permitting the operator to instruct said controller to determine the blood flow in the blood vessel using:
the second path 1 measurement and the second path 2 measurement when the operator selects the third selector switch;
the second path 1 measurement and the first path 2 measurement when the operator selects the first selector switch; and
the second path 2 measurement and the first path 1 measurement when the operator selects the second selector switch;

a fifth selector switch permitting the operator to instruct said controller to determine the blood flow using the first path 1 measurement and the first path 2 measurement after the operator has used said first selector switch to instruct said meter to perform a second path 1 measurement;

a sixth selector switch permitting the operator to instruct said controller to determine the blood flow using the second path 1 measurement and the first path 2 measurement after the operator has used said first selector switch to instruct said meter to perform a second path 1 measurement;

a seventh selector switch permitting the operator to instruct said controller to determine the blood flow using the first path 2 measurement and the first path 1 measurement after the operator has used said second selector switch to instruct said meter to perform a second path 2 measurement; and an eighth selector switch permitting the operator to instruct said controller to determine the blood flow using the second path 2 measurement and the first path 1 measurement after the operator has used said second selector switch to instruct said meter to perform a second path 2 measurement.

15. An ocular blood-flow meter comprising:
an optical system configured and positioned to apply measuring light to a blood vessel of a subject eye, and to receive light scattered by the blood vessel of the subject eye;
a mechanism configured and positioned to change the direction in which the measuring light is applied to the blood vessel or the direction in which the scattered light is received by at least a portion of said optical system so as to enable a plurality of measurements of the blood flow in the blood vessel using measuring light applied to the blood vessel in different directions or using scattered light received by at least a portion of said optical system in different directions;
a controller configured to perform the plurality of measurements of the blood flow in the blood vessel using the measuring light being applied to the blood vessel in different directions and scattered by the blood vessel or using the scattered light received by at least a portion of said optical system in different directions,
wherein said controller is also configured to perform a re-measurement operation to re-measure the blood flow in the blood vessel using the measuring light being applied to the blood vessel in a desired direction and then scattered by the blood vessel or using scattered light received by at least a portion of said optical system in a desired direction,
wherein said controller is also configured to determine whether a re-measurement operation is required; and
an output device connected to said controller,
wherein said output device is configured to present information to an operator indicating whether re-measurement is required in response to said controller determining that a re-measurement operation is required.

16. An ocular blood-flow meter according to claim 15,
further comprising a device configured and positioned to receive the scattered light from said optical system,
wherein said device outputs received-light signals containing information on blood flow in the blood vessel in response to receiving measuring light being applied to the blood vessel in different directions and scattered by the blood vessel or in response to receiving scattered light that has been received by at least a portion of said optical system in different directions,
wherein said controller is connected to said device and receives the received-light signals and performs the plurality of measurements and the re-measurement operation using the received-light signals,
wherein said output device comprises a display device configured to display a representation of the received-light signals or information concerning the blood flow in the blood vessel,
wherein said controller is configured to determine the quality of the received-light signals obtained by performing each of the plurality of measurements, and to compare the quality of the received-light signals so as to determine whether the re-measurement operation is required; and
wherein said display device displays information that a re-measurement operation is required in response to said controller determining that the re-measurement operation is required.

17. An ocular blood-flow meter according to claim 16,
wherein said controller determines the quality of the received-light signal obtained by performing a re-measurement operation, and compares the quality of the received-light signal before the re-measurement operation with the quality of the received-light signal after the re-measurement operation, so as to calculate the blood flow based on the received-light signal having the better quality.

18. The ocular blood-flow meter according to claim 16, wherein said mechanism changes the position of said device so as to change the direction in which the scattered light is received by at least a portion of said optical system.

19. An ocular blood-flow meter according to claim 15,
wherein said optical system comprises:
a measuring light source; and
a lens,
wherein said mechanism is positioned between said measuring light source and said lens and comprises:
a retractable optical path switching mirror; and
a stationary mirror, and
wherein said optical path switching mirror is retractable out of and insertable into the path of measuring light from said measuring light source and said lens, wherein when said optical path switching mirror is in the optical path from said measuring light source to said lens, said optical path switching mirror reflects measuring light from said measuring light source to said stationary mirror, which reflects the measuring light to a first portion of said lens, and wherein when said optical path switching mirror is out of the optical path from said measuring light source to said lens, measuring light from said measuring light source is projected directly to a second portion of said lens, whereby said mechanism changes the direction in which the measuring light is applied to the blood vessel.

20. The ocular blood-flow meter according to claim 15, further comprising an input device connected to said controller,
    wherein said input device comprises a selection switch panel on which first, second, and third switches are disposed to select only a first direction, only a second direction, and both said first and second directions, respectively, in which the operator desires the measuring light to be applied to the blood vessel and then scattered by the blood vessel or to select only a first direction, only a second direction, and both said first and second directions, respectively, in which the operator desires that the scattered light be received by at least a portion of said optical system.

21. The ocular blood-flow meter according to claim 15, wherein said controller processes the received-light signals over time,
    wherein said controller determines an evaluation value over time that represents the quality of each received-light signal, by comparing the evaluation value for each received-light signal with a reference value,
    wherein said controller determines that a re-measurement operation is required when the evaluation value for a received-light signal is below the reference value.

22. The ocular blood-flow meter according to claim 21, wherein said controller processes each received-light signal over time by performing a fast Fourier Transform operation on each received-light signal to produce a fast Fourier Transform waveform over time for each received-light signal, from which said controller determines an evaluation value for each received-light signal.

23. An ocular blood-flow meter comprising:
    optical means for applying measuring light to a blood vessel of a subject eye, and for receiving light scattered by the blood vessel of the subject eye;
    direction-changing means for changing the direction in which the measuring light is applied to the blood vessel or the direction in which the scattered light is received by at least a portion of said optical means so as to enable a plurality of measurements of the blood flow in the blood vessel using measuring light applied to the blood vessel in different directions or using scattered light received by at least a portion of said optical means in different directions;
    signal-outputting means for outputting a received-light signal containing information on blood flow in the blood vessel in response to receiving the scattered light from said optical means;
    control means for performing the plurality of measurements of the blood flow in the blood vessel using the received-light signal generated from measuring light being applied to the blood vessel in different directions and scattered by the blood vessel or generated from the scattered light received by at least a portion of said optical means in different directions,
        wherein said control means comprises means for performing a re-measurement operation to re-measure the blood flow in the blood vessel using a received-light signal generated from measuring light being applied to the blood vessel in a desired direction and then scattered by the blood vessel or generated from the scattered light received by at least a portion of said optical means in a desired direction in response to an instruction by an operator to perform a re-measurement operation in the desired direction; and
    input means for enabling an operator to select a re-measurement operation to re-measure the blood flow in the blood vessel using a received-light signal generated from measuring light being applied to the blood vessel in a desired direction and then scattered by the blood vessel or generated from the scattered light received by at least a portion of said optical means in a desired direction,
        wherein said input means comprises means for instructing said control means to perform the selected re-measurement operation selected by the operator.

24. An ocular blood-flow meter according to claim 23, wherein said input means comprises selector means for enabling the operator to select a desired measurement result from a plurality of measurement results obtained in the desired direction in which the re-measurement operation is performed.

25. An ocular blood-flow meter according to claim 23, further comprising:
    tracking means for tracking movement of the subject eye; and
    display means for displaying tracking information obtained by said tracking means.

26. An ocular blood-flow meter according to claim 23, further comprising:
    measurement means configured to measure blood vessel size; and
    display means for displaying the measurement results obtained by said measurement means.

27. An ocular blood-flow meter according to claim 23, further comprising display means for presenting to the operator a plurality of measurement results using the received light signal output from said signal-outputting device so as to provide information to the operator to enable the operator to determine whether the re-measurement operation is required.

28. The ocular blood-flow meter according to claim 23, wherein said optical means comprises:
    measuring light source means for emitting measuring light; and
    means for refracting said measuring light,
    wherein said direction-changing means for reflecting the measuring light incident thereon; and
        stationary reflecting means for reflecting the measuring light received from said movable reflecting means to said means for refracting when said movable reflecting means is in the optical path from said measuring light source means to said means for refracting,
    wherein said movable reflecting means comprises means for changing the direction in which the measuring light is applied to the blood vessel by moving out of or into the path of measuring light from said measuring light source means and said refracting means.

29. The ocular blood-flow meter according to claim 23, wherein said direction-changing means comprises means for changing the position of said signal outputting means so as to change the direction in which the scattered light is received by at least a portion of said optical means.

30. The ocular blood-flow meter according to claim 23, wherein said input means comprises first, second, and third selection means for selecting only a first direction, only a second direction, and both said first and second directions, respectively, in which the operator desires the measuring light to be applied to the blood vessel and then scattered by the blood vessel or to select only a first direction, only a second direction, and both said first and second directions, respectively, in which the operator desires that the scattered light be received by at least a portion of said optical means.

31. The ocular blood-flow meter according to claim 23, further comprising:
    tracking means for tracking movement of the subject eye,
        wherein said tracking means comprises:
            blood-vessel image forming means for producing a blood-vessel image of the blood vessel; and
            blood-vessel-image-signal producing means for producing a signal representing the blood-vessel image,
        wherein said control means comprises means for determining the position and amount of movement of the blood-vessel image from the signal produced by said tracking means,
        wherein the amount of movement of the blood-vessel image that is determined by said control means is indicative of the quality of the tracking performed by said tracking means; and
    display means for displaying data,
        wherein said control means comprises means for processing the received-light signal over time and determining an evaluation value over time that represents the quality of the received-light signal,
        wherein said control means comprises means for calculating the variation in the frequency of over time of the processed received-light signal,
        wherein said display means comprises means for displaying a first graph of the processed received-light signal over time processed by said control means,
        wherein said display means comprises means for displaying a second graph of the evaluation value determined by said control means before and during measurement of the blood flow in the blood vessel,
        wherein said display means comprises means for displaying a third graph representing the variation over time in the amount of movement of the blood-vessel image during measurement of the blood flow in the blood vessel, and
        wherein said display means comprises means for displaying a fourth graph representing the variation in the frequency of over time of the processed received-light signal after measurement of the blood flow in the blood vessel.

32. The ocular blood-flow meter according to claim 31, wherein said control means comprises means for processing the received-light signal over time by performing a fast Fourier Transform operation on the received-light signal to produce a fast Fourier Transform waveform over time,
    wherein said display means comprises means for displaying the fast Fourier Transform waveform over time as the first graph,
    wherein said control means also comprises means for determining the maximum frequency when the power spectrum of the fast Fourier Transform waveform exceeds a predetermined threshold, and
    wherein said display means also comprises means for displaying the variation in the frequency over time of the power spectrum of the fast Fourier Transform waveform as the fourth graph.

33. The ocular blood-flow meter according to claim 23, further comprising:
    image forming means forming a blood-vessel image,
    wherein said control means comprises:
        means for determining variations in the amount of movement over time of the blood-vessel image, and
        means for processing the received-light signal to produce a processed received-light signal for determining the frequency over time of the processed received-light signal, and
    wherein said meter further comprises display means for displaying the variations in the amount of movement over time of the blood-vessel image, and
    wherein said display means comprises means for displaying the frequency over time of the processed received-light signal.

34. The ocular blood-flow meter according to claim 23, wherein said control means comprises:
    means for processing the received-light signal over time,
    means for determining an evaluation value over time that represents the quality of the received-light signal generated from measuring light being applied to the blood vessel in a first direction and scattered by the blood vessel or generated from the scattered light received by at least a portion of said optical means in the first direction, and
    means for determining an evaluation value over time that represents the quality of the received-light signal generated from measuring light being applied to the blood vessel in a second direction and scattered by the blood vessel or generated from the scattered light received by at least a portion of said optical means in the second direction,
    wherein said meter further comprises display means for displaying the evaluation values over time associated with the first and second directions, simultaneously.

35. The ocular blood-flow meter according to claim 34, further comprising:
    image forming means forming a blood-vessel image,
    wherein said meter further comprises:
        means for capturing the blood-vessel image at different times during the plurality of measurements of the blood flow to produce a plurality of blood-vessel images of the same blood vessel over time,
        tracking means for optically tracking the blood vessel during movement of the blood vessel so that the blood-vessel image of the blood vessel formed by said image forming means is positioned at substantially the same position over time during the plurality of measurements and during a re-measurement operation when tracking is properly performed,
    wherein when tracking by said tracking means is not properly performed, the position of the blood-vessel image changes over time,
    wherein said display means comprises means for displaying in an overlapping manner the plurality of captured blood-vessel images while receiving the light generated from measuring light being applied to the blood vessel in the first direction and scattered by the blood vessel or generated from the scattered light received by at least a portion of said optical means in the first direction, wherein the thickness of the displayed, overlapped blood vessel images associated with the first direction is greater when said tracking means performs tracking improperly than when said tracking means performs tracking properly, wherein said display means comprises means for displaying in an overlapping manner the plurality of captured blood-vessel images while receiving the light generated from measuring light being applied to the blood vessel in the second direction and scattered by blood vessel or generated from the scattered light received by at least a portion of said optical means in the second direction, and wherein the thickness of the displayed, overlapped blood-vessel images associated with the second direction is greater when said tracking means performs tracking improperly than when said tracking means performs tracking properly.

36. The ocular blood-flow meter according to claim 23 or 35, wherein a measurement operation performed using received-light signal generated from measuring light being applied to the blood vessel in the first direction and scattered by the blood vessel or generated from the scattered light received by at least a portion of said optical means in the first direction is denoted as the first path 1 measurement, wherein a re-measurement operation performed using a received-light signal generated from measuring light being applied to the blood vessel in the first direction and scattered by the blood vessel or generated from the scattered light received by at least a portion of said optical means in the first direction is denoted as the second path 1 measurement, wherein a measurement operation performed using a received-light signal generated from measuring light being applied to the blood vessel in the second direction and scattered by the blood vessel or generated from the scattered light received by at least a portion of said optical means in the second direction is denoted as the first path 2 measurement, wherein a re-measurement operation performed using a received-light signal generated from measuring light being applied to the blood vessel in the second direction and scattered by the blood vessel or generated from the scattered light received by at least a portion of said optical means in the second direction is denoted as the second path 2 measurement, wherein said input means comprises:
first selector means for permitting the operator to instruct said meter to perform a second path 1 measurement;
second selector means for permitting the operator to instruct said meter to perform a second path 2 measurement;
third selector means for permitting the operator to instruct said meter to perform a re-measurement operation using a received-light signal generated from measuring light being applied to the blood vessel in the first and second directions and scattered by the blood vessel or generated from the scattered light received by at least a portion of said optical means in the first and second directions;

fourth selector means for permitting the operator to instruct said control means to determine the blood flow in the blood vessel using:
the second path 1 measurement and the second path 2 measurement when the operator selects the third selector means;
the second path 1 measurement and the first path 2 measurement when the operator selects the first selector means;
the second path 2 measurement and the first path 1 measurement when the operator selects the second selector means;
fifth selector means for permitting the operator to instruct said control means to determine the blood flow using the first path 1 measurement and the first path 2 measurement after the operator has used said first selector means to instruct said meter to perform a second path 1 measurement;
sixth selector means for permitting the operator to instruct said control means to determine the blood flow using the second path 1 measurement and the first path 2 measurement after the operator has used said first selector means to instruct said meter to perform a second path 1 measurement;
seventh selector means for permitting the operator to instruct said control means to determine the blood flow using the first path 2 measurement and the first path 1 measurement after the operator has used said second selector means to instruct said meter to perform a second path 2 measurement; and
eighth selector means for permitting the operator to instruct said control means to determine the blood flow using the second path 2 measurement and the first path 1 measurement after the operator has used said second selector means to instruct said meter to perform a second path 2 measurement.

37. An ocular blood-flow meter comprising:
optical means for applying measuring light to a blood vessel of a subject eye, and for receiving light scattered by the blood vessel of the subject eye;
direction-changing means for changing the direction in which the measuring light is applied to the blood vessel or the direction in which the scattered light is received by at least a portion of said optical means so as to enable a plurality of measurements of the blood flow in the blood vessel using measuring light applied to the blood vessel in different directions or using scattered light received by at least a portion of said optical means in different directions;
control means for performing the plurality of measurements of the blood flow in the blood vessel using the measuring light being applied to the blood vessel in different directions and scattered by the blood vessel or using the scattered light received by at least a portion of said optical means in different directions,
wherein said control means comprises means for performing a re-measurement operation to re-measure the blood flow in the blood vessel using measuring light being applied to the blood vessel in a desired direction and then scattered by the blood vessel or using scattered light received by at least a portion of said optical means in a desired direction,
wherein said control means also comprises means for determining whether a re-measurement operation is required; and
output means for presenting information to an operator indicating whether re-measurement is required in response to said control means determining that a re-measurement operation is required.

38. An ocular blood-flow meter according to claim 37, further comprising signal-outputting means for outputting received-light signals containing information on blood flow in the blood vessel in response to receiving measuring light being applied to the blood vessel in different directions and scattered by the blood vessel or in response to receiving scattered light that has been received by at least a portion of said optical means in different directions, wherein said control means comprises means for receiving the received-light signals and performing the plurality of measurements and the re-measurement operation using the received-light signals, wherein said signal-outputting means comprises display means for displaying a representation of the received-light signals or information concerning the blood flow in the blood vessel, wherein said control means also comprises means for determining the quality of the received-light signals obtained by performing each of the plurality of measurements, and for comparing the quality of the received-light signals so as to determine whether the re-measurement operation is required; and wherein said display means comprises means for displaying information that a re-measurement operation is required in response to said control means determining that the re-measurement operation is required.

39. An ocular blood-flow meter according to claim 38, wherein said control means comprises means for determining the quality of the received-light signal obtained by performing a re-measurement operation, and for comparing the quality of the received-light signal before the re-measurement operation with the quality of the received-light signal after the re-measurement operation, so as to calculate the blood flow based on the received-light signal having the better quality.

40. An ocular blood-flow meter according to claim 37, wherein said optical means comprises:
    measuring light source means for emitting the measuring light; and
    refracting means for refracting the measuring light from said measuring light source means,
wherein said direction-changing means comprises:
    movable reflecting means for reflecting the measuring light from said measuring light source means; and
    stationary reflecting means for reflecting measuring light reflected by said movable reflecting means to said refracting means when said movable reflecting means is positioned in the optical path from said measuring light source to said refracting means, and
wherein said movable reflecting means is retractable out of and insertable into the path of measuring light from said measuring light source means and said refracting means so as to change the direction in which the measuring light is applied to the blood vessel.

41. The ocular blood-flow meter according to claim 37, wherein said direction-changing means comprises means for changing the position of said signal-outputting means so as to change the direction in which the scattered light is received by at least a portion of said optical means.

42. The ocular blood-flow meter according to claim 37, further comprising input means for permitting an operator to input selections into said meter, wherein said input means comprises first, second, and third selector means for selecting only a first direction, only a second direction, and both said first and second directions, respectively, in which the operator desires the measuring light to be applied to the blood vessel and then scattered by the blood vessel or to select only a first direction, only a second direction, and both said first and second directions, respectively, in which the operator desires that the scattered light be received by at least a portion of said optical means.

43. The ocular blood-flow meter according to claim 37, wherein said control means comprises:
    means for processing the received-light signals over time;
    means for determining an evaluation value over time that represents the quality of each received-light signal, by comparing the evaluation value for each received-light signal with a reference value; and
    means for determining that a re-measurement operation is required when the evaluation value for a received-light signal is below the reference value.

44. The ocular blood-flow meter according to claim 43, wherein said control means further comprises means for processing each received-light signal over time by performing a fast Fourier Transform operation on each received-light signal to produce a fast Fourier Transform waveform over time for each received-light signal, from which said control means determines an evaluation value for each received-light signal.

45. A method of measuring ocular blood flow in an ocular blood vessel comprising the steps of:
    applying measuring light to a blood vessel of a subject eye;
    receiving light scattered by the blood vessel of the subject eye;
    changing the direction in which the measuring light is applied to the blood vessel in said applying step or the direction in which the scattered light is received in said receiving step so as to enable the performing of a plurality of measurements of the blood flow in the blood vessel using measuring light applied to the blood vessel in different directions or using scattered light received in different directions;
    outputting a received-light signal containing information on blood flow in the blood vessel generated from the scattered light received in said receiving step;
    performing the plurality of measurements of the blood flow in the blood vessel using the received-light signal generated from measuring light being applied to the blood vessel in different directions and scattered by the blood vessel or generated from the scattered light received in different directions; and
    performing a re-measurement operation to re-measure the blood flow in the blood vessel using a received-light signal generated from measuring light being applied to the blood vessel in a desired direction and then scattered by the blood vessel or generated from the scattered light received in a desired direction in response to an instruction by an operator to perform a re-measurement operation in the desired direction.

46. A method according to claim 45, further comprising the steps of:
    tracking movement of the subject eye; and
    displaying tracking information obtained by said tracking step.

47. A method according to claim 45, further comprising the steps of:
    measuring blood vessel size; and displaying the measurement result obtained by said measuring step.

48. A method according to claim 45, further comprising the step of presenting to the operator a plurality of measurement results using the received light signal output in said signal-outputting step so as to provide information to the operator to enable the operator to determine whether the re-measurement operation is required.

49. A method according to claim 45,
wherein said applying step comprises the steps of:
   emitting measuring light; and
   refracting the measuring light with refracting means,
wherein said direction-changing step comprises the step of:
   changing the position at which the measuring light emitted in said emitting step is incident upon said refracting means.

50. A method according to claim 45, wherein said signal-outputting step is performed by signal-outputting means, wherein said direction-changing step comprises the step of changing the position of said signal-outputting means.

51. A method according to claim 45, further comprising the steps of:
   performing a re-measurement operation in only a first direction in response to the operator actuating first selection means;
   performing a re-measurement operation in only a second direction in response to the operator actuating second selection means; and
   performing a re-measurement operation in both the first and second directions in response to the operator actuating third selection means.

52. A method according to claim 45, further comprising the steps of:
   tracking movement of the subject eye comprising the steps of:
      forming a blood-vessel image of the blood vessel; and
      producing a signal representing the blood-vessel image; and
      determining the position and amount of movement of the blood-vessel image from the signal produced by said tracking producing step,
         wherein the amount of movement of the blood-vessel image that is determined by said determining step is indicative of the quality of the tracking performed by said tracking step;
   processing the received-light signal over time and determining an evaluation value over time that represents the quality of the received-light signal;
   calculating the variation in the frequency of over time of the processed received-light signal;
   displaying a first graph of the processed received-light signal over time;
   displaying a second graph of the evaluation value determined before and during measurement of the blood flow in the blood vessel;
   displaying a third graph representing the variation over time in the amount of movement of the blood-vessel image during measurement of the blood flow in the blood vessel; and
   displaying a fourth graph representing the variation in the frequency of over time of the processed received-light signal after measurement of the blood flow in the blood vessel.

53. A method according to claim 52, further comprising the steps of:
   processing the received-light signal over time by performing a fast Fourier Transform operation on the received-light signal to produce a fast Fourier Transform waveform over time;
   displaying the fast Fourier Transform waveform over time as the first graph;
   determining the maximum frequency when the power spectrum of the fast Fourier Transform waveform exceeds a predetermined threshold; and
   displaying the variation in the frequency over time of the power spectrum of the fast Fourier Transform waveform as the fourth graph.

54. A method according to claim 45, further comprising the steps of:
   forming a blood-vessel image;
   determining variations in the amount of movement over time of the blood-vessel image;
   processing the received-light signal to produce a processed received-light signal for determining the frequency over time of the processed received-light signal;
   displaying the variations in the amount of movement over time of the blood-vessel image; and
   displaying the frequency over time of the processed received-light signal.

55. A method according to claim 45, further comprising the steps of:
   processing the received-light signal over time;
   determining an evaluation value over time that represents the quality of the received-light signal generated from measuring light being applied to the blood vessel in a first direction and scattered by the blood vessel or generated from the scattered light received in the first direction;
   determining an evaluation value over time that represents the quality of the received-light signal generated from measuring light being applied to the blood vessel in a second direction and scattered by the blood vessel or generated from the scattered light received in the second direction; and
   displaying the evaluation values over time associated with the first and second directions, simultaneously.

56. A method according to claim 55, further comprising the steps of:
   forming a blood-vessel image;
   capturing the blood vessel image at different times during the plurality of measurements of the blood flow to produce a plurality of blood-vessel images of the same blood vessel over time;
   optically tracking the blood vessel during movement of the blood vessel so that the blood-vessel image of the blood vessel is positioned at substantially the same position over time during the plurality of measurements and during a re-measurement operation when tracking is properly performed,
      wherein when tracking is not properly performed, the position of the blood-vessel image changes over time,
   displaying in an overlapping manner the plurality of captured blood vessel images while receiving the light generated from measuring light being applied to the blood vessel in the first direction and scattered by the blood vessel or generated from the scattered light received in the first direction;

displaying a greater thickness for the displayed, overlapped blood-vessel images associated with the first direction when tracking is performed improperly than when tracking is performed properly;

displaying in an overlapping manner the plurality of captured blood-vessel images while receiving the light generated from measuring light being applied to the blood vessel in the second direction and scattered by the blood vessel or generated from the scattered light received in the second direction; and displaying a greater thickness for the displayed, overlapped blood-vessel images associated with the second direction when tracking is performed improperly than tracking is performed properly.

57. A method according to claim 45 or 56, wherein a measurement operation performed using a received-light signal generated from measuring light being applied to the blood vessel in the first direction and scattered by the blood vessel or generated from the scattered light received in the first direction is denoted as the first path 1 measurement, wherein a re-measurement operation performed using a received-light signal generated from measuring light being applied to the blood vessel in the first direction and scattered by the blood vessel or generated from the scattered light received in the first direction is denoted as the second path 1 measurement, wherein a measurement operation performed using a received-light signal generated from measuring light being applied to the blood vessel in the second direction and scattered by the blood vessel or generated from the scattered light received in the second direction is denoted as the first path 2 measurement, wherein a re-measurement operation performed using a received-light signal generated from measuring light being applied to the blood vessel in the second direction and scattered by the blood vessel or generated from the scattered light received in the second direction is denoted as the second path 2 measurement, wherein said method further comprises the steps of:

performing a second path 1 measurement in response to the operator actuating first selector means;

performing a second path 2 measurement in response to the operator actuating second selector means;

performing a re-measurement operation using a received-light signal generated from measuring light being applied to the blood vessel in the first and second directions and scattered by the blood vessel or generated form the scattered light received in the first and second directions in response to the operator actuating third selector means;

determining the blood flow in the blood vessel in response to the operator actuating fourth selector means using:

the second path 1 measurement and the second path 2 measurement when the operator selects the third selector means;

the second path 1 measurement and the first path 2 measurement when the operator selects the first selector means; and the second path 2 measurement and the first path 1 measurement when the operator selects the second selector means;

determining the blood flow using the first path 1 measurement and the first path 2 measurement after the operator has used said first selector means to instruct said meter to perform a second path 1 measurement in response to the operator actuating fifth selector means;

determining the blood flow using the second path 1 measurement and the first path 2 measurement after the operator has used said first selector means to instruct said meter to perform a second path 1 measurement in response to the operator actuating sixth selector means;

determining the blood flow using the first path 2 measurement and the first path 1 measurement after the operator has used said second selector means to instruct said meter to perform a second path 2 measurement in response to the operator actuating seventh selector means; and determining the blood flow using the second path 2 measurement and the first path 1 measurement after the operator has used said second selector means to instruct said meter to perform a second path 2 measurement in response to the operator actuating eighth selector means.

58. A method of determining the ocular blood flow in an ocular blood vessel comprising the steps of:

applying measuring light to a blood vessel of a subject eye;

receiving light scattered by the blood vessel of the subject eye;

changing the direction in which the measuring light is applied to the blood vessel in said applying step or the direction in which the scattered light is received in said receiving step so as to enable a plurality of measurements of the blood flow in the blood vessel using measuring light applied to the blood vessel in different directions or using scattered light received in different directions;

performing the plurality of measurements of the blood flow in the blood vessel using the measuring light being applied to the blood vessel in different directions and scattered by the blood vessel or using the scattered light received in different directions;

performing a re-measurement operation to re-measure the blood flow in the blood vessel using measuring light being applied to the blood vessel in a desired direction and then scattered by the blood vessel or using scattered light received in a desired direction;

determining whether a re-measurement operation is required; and presenting information to an operator indicating whether re-measurement is required in response to said determining step determining that a re-measurement operation is required.

59. A method according to claim 58, further comprising the steps of:

outputting received-light signals containing information on blood flow in the blood vessel in response to receiving measuring light being applied to the blood vessel in different directions and scattered by the blood vessel or in response to receiving scattered light that has been received in different directions;

performing the plurality of measurements and the re-measurement operation using the received-light signals;

displaying a representation of the received-light signals or information concerning the blood flow in the blood vessel;

determining the quality of the received-light signals obtained by performing each of the plurality of measurements, and comparing the quality of the received-light signals so as to determine whether the re-measurement operation is required; and displaying information that a re-measurement operation is required in response to determining that the re-measurement operation is required.

60. A method according to claim 59, further comprising the steps of:

determining the quality of the received-light signal obtained by performing a re-measurement operation, and comparing the quality of the received-light signal before the re-measurement operation with the quality of the received-light signal after the re-measurement operation, so as to calculate the blood flow based on the received-light signal having the better quality.

61. A method according to claim 58, wherein said applying step comprises the steps of:
emitting measuring light; and
refracting the measuring light with refracting means, wherein said direction-changing step comprises the step of:
changing the position at which the measuring light emitted in said emitting step is incident upon said refracting means.

62. A method according to claim 58, wherein said signal-outputting step is performed by signal-outputting means, wherein said direction-changing step comprises the step of changing the position of the signal-outputting means so as to change the direction in which the scattered light is received in said receiving step.

63. A method according to claim 58, further comprising the steps of:

performing a re-measurement operation in only a first direction in response to the operator actuating first selection means;

performing a re-measurement operation in only a second direction in response to the operator actuating second selection means; and performing a re-measurement operation in both the first and second directions in response to the operator actuating third selection means.

64. A method according to claim 58, further comprising the steps of:

processing the received-light signals over time;

determining an evaluation value over time that represents the quality of each received-light signal, by comparing the evaluation value for each received-light signal with a reference value; and determining that a re-measurement operation is required when the evaluation value for a received-light signal is below the reference value.

65. A method according to claim 64, further comprising the steps of:

processing each received-light signal over time by performing a fast Fourier Transform operation on each received-light signal to produce a fast Fourier Transform waveform over time for each received-light signal, from which said evaluation value determining step determines an evaluation value for each received-light signal.

66. An ocular blood-flow meter comprising:

an optical system for emitting a measuring light beam to a blood vessel of an eye to be examined, and for receiving the scattered light beam from the blood vessel;

a direction changing mechanism for changing the emitting direction of the measuring light beam to the blood vessel or the receiving direction of the scattered light beam from the blood vessel so as to enable a plurality of measurements of the blood flow from different directions;

a light-receiving device for receiving the scattered light from said optical system;

a controller connected to said device for receiving the signal representing the received scattered light from the light-receiving device and for performing the plurality of measurements from different directions determined by said direction changing mechanism;

an input device electrically coupled to said controller for enabling an operator to select a re-measurement in at least a desired direction and for instructing said controller to perform the selected re-measurement operation selected by the operator.

* * * * *

UNITED STATES PATENT AND TRADEMARK OFFICE
CERTIFICATE OF CORRECTION

PATENT NO. : 6,699,198 B2
DATED : March 2, 2004
INVENTOR(S) : Yasuyuki Numajiri

It is certified that error appears in the above-identified patent and that said Letters Patent is hereby corrected as shown below:

Column 1,
Line 28, "a indicates" should read -- $\alpha$ indicates --.

Column 2,
Line 25, "determine" should read -- determined --.

Column 10,
Line 22, "become" should read -- becomes --.

Column 16,
Line 54, "which" should read -- in which --.

Column 21,
Line 55, "comprising" should read -- comprising: --.
Line 59, "time" should read -- times --.

Column 35,
Line 14, "tracking" should read -- when tracking --.

Signed and Sealed this

Fifth Day of October, 2004

JON W. DUDAS
*Director of the United States Patent and Trademark Office*